(12) United States Patent
Mazess et al.

(10) Patent No.: US 6,215,846 B1
(45) Date of Patent: Apr. 10, 2001

(54) DENSITOMETRY ADAPTER FOR COMPACT X-RAY FLUOROSCOPY MACHINE

(75) Inventors: Richard B. Mazess; David L. Ergun; Joseph P. Bisek, all of Madison, WI (US)

(73) Assignee: Lunar Corporation, Madison, WI (US)

( * ) Notice: Subject to any disclaimer, the term of this patent is extended or adjusted under 35 U.S.C. 154(b) by 0 days.

(21) Appl. No.: 09/281,518

(22) Filed: Mar. 30, 1999

Related U.S. Application Data

(63) Continuation-in-part of application No. 09/006,358, filed on Jan. 13, 1998, which is a continuation-in-part of application No. PCT/US97/02770, filed on Feb. 21, 1997.
(60) Provisional application No. 60/080,164, filed on Mar. 13, 1998, and provisional application No. 60/011,993, filed on Feb. 21, 1996.

(51) Int. Cl.[7] .................................................... G01N 23/04
(52) U.S. Cl. ........................................... 378/62; 378/98.4
(58) Field of Search ................................. 378/7, 86, 87, 378/98.4, 62

(56) References Cited

U.S. PATENT DOCUMENTS

| | | |
|---|---|---|
| 4,829,549 | 5/1989 | Vogel et al. ............................. 378/55 |
| 5,042,489 | 8/1991 | Wiener et al. .................... 128/661.03 |
| 5,336,880 | 8/1994 | Leclerc et al. ......................... 250/214 |
| 5,416,818 | 5/1995 | Takahashi et al. ................... 378/98.7 |
| 5,878,108 * | 3/1999 | Baba et al. ........................... 378/98.4 |
| 5,903,008 * | 5/1999 | Li ..................................... 250/363.04 |
| 5,905,809 * | 5/1999 | Timmer ................................. 382/131 |
| 6,061,419 * | 5/2000 | Hsieh et al. .............................. 378/4 |
| 6,104,777 * | 8/2000 | Darboux et al. ........................ 378/62 |

* cited by examiner

*Primary Examiner*—David V. Bruce
*Assistant Examiner*—Allen C. Ho
(74) *Attorney, Agent, or Firm*—Quarles & Brady LLP

(57) ABSTRACT

An accessory for fluoroscopy equipment is provided to support the x-ray tube and detector on a pedestal with respect to a patient limb for quantitative bone densitometry measurement. Software loaded into the associated digital imaging fluoroscopy equipment provides necessary correction of the images for the quantitative accuracy needed for bone densitometry. Alternatively, a specialized detector or extremely low form factor image intensifier may be inserted in the pedestal to be used in lieu of the fluoroscopy equipment detector. A similar software correction is performed on an associated computer when a separate detector must be used.

10 Claims, 13 Drawing Sheets

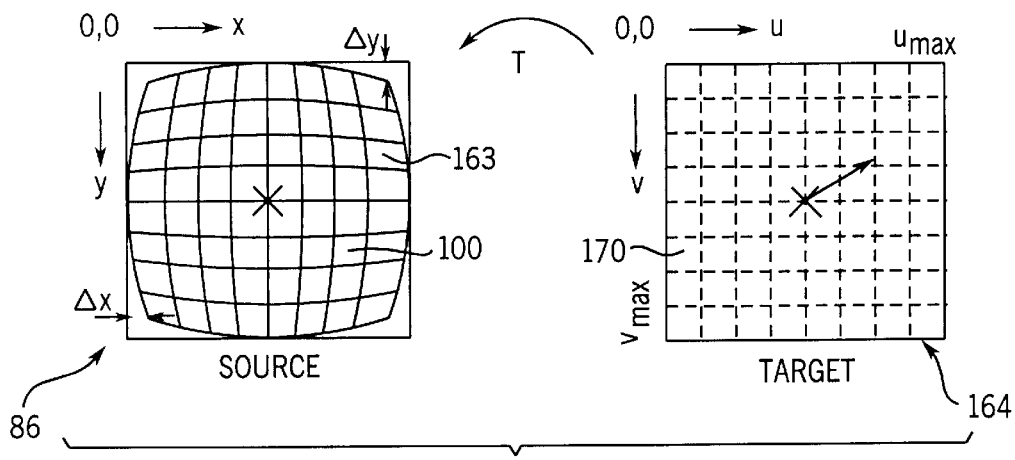
FIG. 19
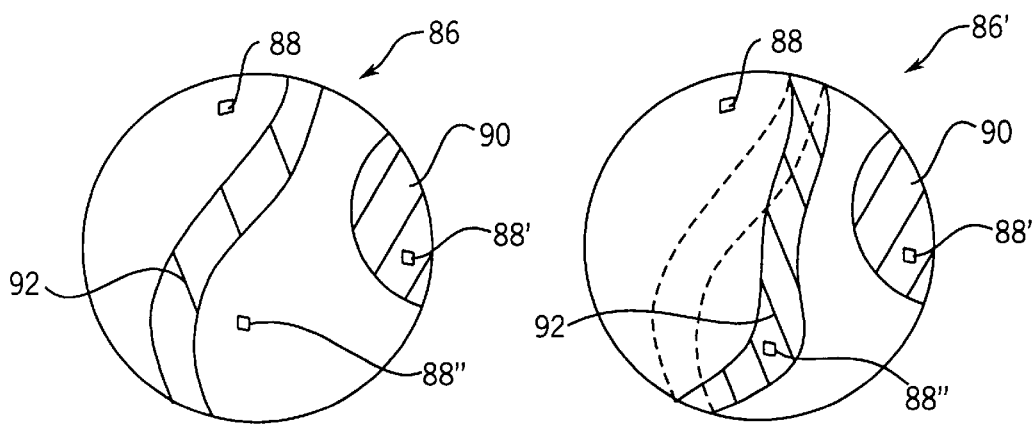
FIG. 7
FIG. 8
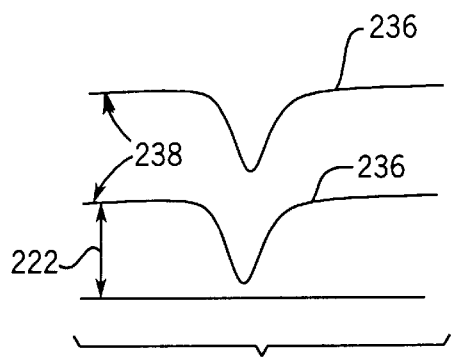
FIG. 24

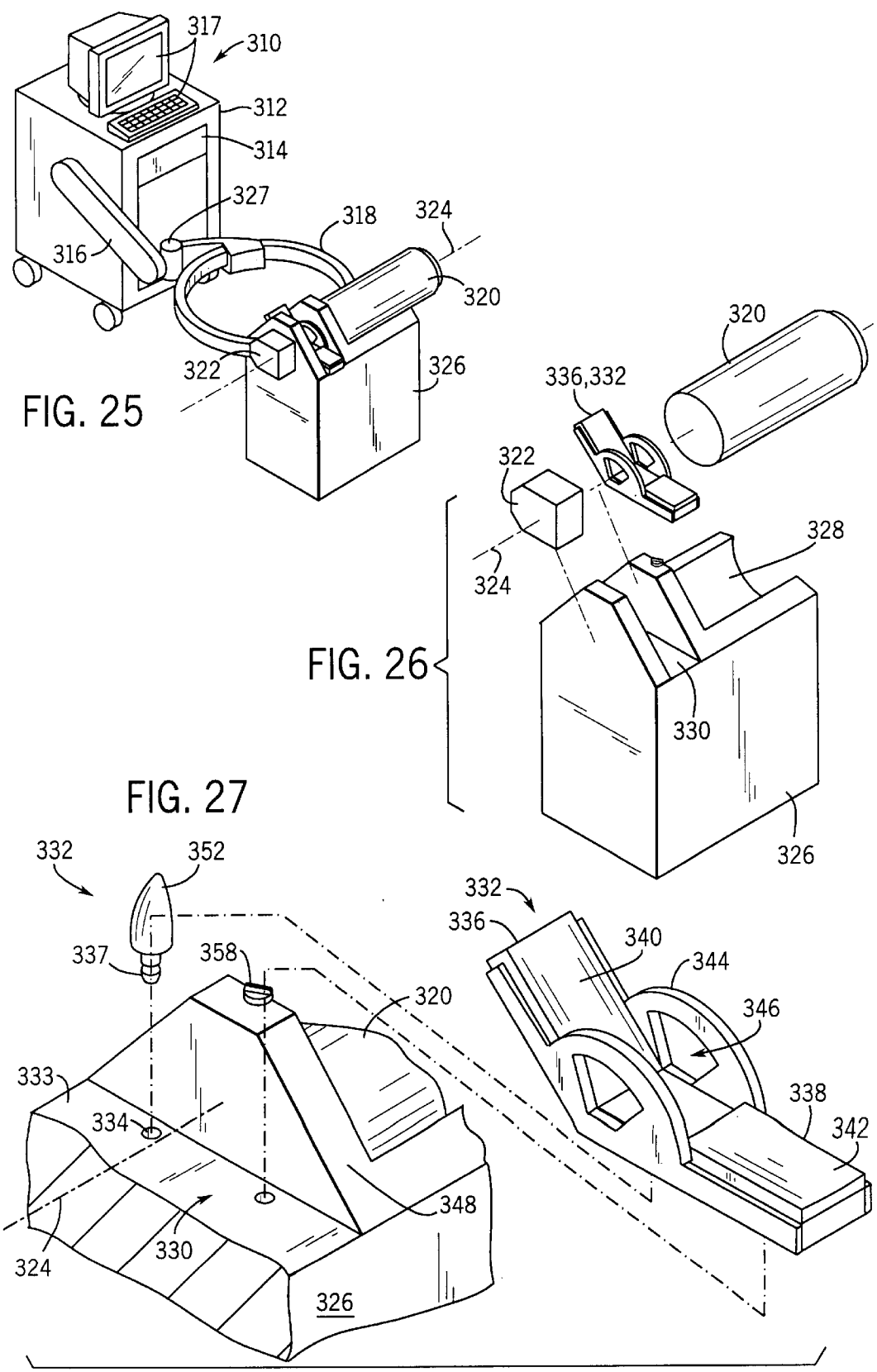

DENSITOMETRY ADAPTER FOR COMPACT X-RAY FLUOROSCOPY MACHINE

CROSS-REFERENCE TO RELATED APPLICATIONS

This application is based on U.S. provisional application Ser. No. 60/080,164 filed Mar. 31, 1998 and is a continuation in part of U.S. application Ser. No. 09/006,358 filed Jan. 13, 1998 which is a continuation-in -part of PCT Application 97/02770 designating the United States filed Feb. 21, 1997 claiming the benefit of provisional application Ser. No. 60/011,993 filed Feb. 21, 1996. This provisional application is incorporated by reference herein.

STATEMENT REGARDING FEDERALLY SPONSORED RESEARCH OR DEVELOPMENT

FIELD OF THE INVENTION

The invention relates generally to x-ray equipment and in particular to an adapter for bone density measurements as may be used with compact x-ray fluoroscopy equipment used for orthopedic and similar procedures.

BACKGROUND OF THE INVENTION

Portable x-ray fluoroscopy machines provide an x-ray source held in opposition to an electronic image detector, typically on a C-arm, so that x-rays from the x-ray source are received by the image detector. The C-arm may slide through a collar so as to allow it to be rotated to different angles about the patient. Further, the collar may be supported by a pivoting arm providing additional freedom in the positioning of the C-arm.

When the C-arm is correctly positioned, the x-ray source is activated and x-rays pass through the patient to be received by the image detector which provides electronic signals to a video monitor. For larger mobile C-arm systems, the video monitor is typically held on a separate cart or may be suspended from the ceiling on a fixed bracket to be connected to the mobile unit when the mobile unit is in place.

With improvements in electronic hardware and in particular the development of compact image intensifiers and CCD video cameras, it has become possible to build extremely compact mobile C-arm systems. Such systems may make use of increasingly powerful desktop computer technology for image processing and other tasks and may use compact digital printers for producing images.

BRIEF SUMMARY OF THE INVENTION

The present invention provides an adapter that may convert a compact fluoroscopy machine or other mobile x-ray source into a precision quantitative densitometer suitable for measuring bone mass or density such as may be helpful in the treatment and detection of osteoporosis.

The invention provides a stand to be used with a fluoroscopy machine, the stand having a cradle for accurately locating the x-ray source and/or detector with respect to either the patient's forearm or foot. Special software is loaded to the computer of the fluoroscopy machine to operate the fluoroscopy machine in a quantitative dual energy mode and to adapt the fluoroscopy data to densiometric data. For fluoroscopy equipment not providing for digital imaging or that may not be easily operated in a dual energy mode, the invention includes a provision for a separate digital dual energy detector and if necessary an associated processing computer.

Other objects, advantages, and features of the present invention will become apparent from the following specification when taken in conjunction with the accompanying drawings.

BRIEF DESCRIPTION OF THE SEVERAL VIEWS OF THE DRAWINGS

FIGS. 7 and 8 are amplified images such as may be obtained by the system of FIG. 1 showing portions of the image having moving elements and portions having stationary elements;

FIG. 19 is a schematic representation of a distorted image of FIG. 11 and a schematic representation of a corresponding undistorted image showing the variables used in the mathematical transformation of the distorted image to correct for rotation and distortion;

FIG. 24 is a graphical representation of an adjustment of calculated scatter from the image of FIG. 23 based on normalizing points established by the occluder of FIG. 21;

FIG. 25 is a perspective view similar to that of FIG. 1 showing a C-arm system similar to that of FIG. 1 in position on the densitometry cradle of the present invention to provide a beam of x-rays along a horizontal axis across the top of the cradle;

FIG. 26 is a fragmentary exploded view of the x-ray detector and x-ray source of the C-arm system of FIG. 25 removed from the cradle and showing a removable foot positioner also removed from the cradle;

FIG. 27 is an enlarged, fragmentary view of FIG. 26 showing the alternative fitting of a forearm positioner or the foot positioner within a channel of the cradle along the path of x-rays between the x-ray source and x-ray detector;

DETAILED DESCRIPTION OF THE INVENTION

C-arm Support Mechanism

Figure 1:
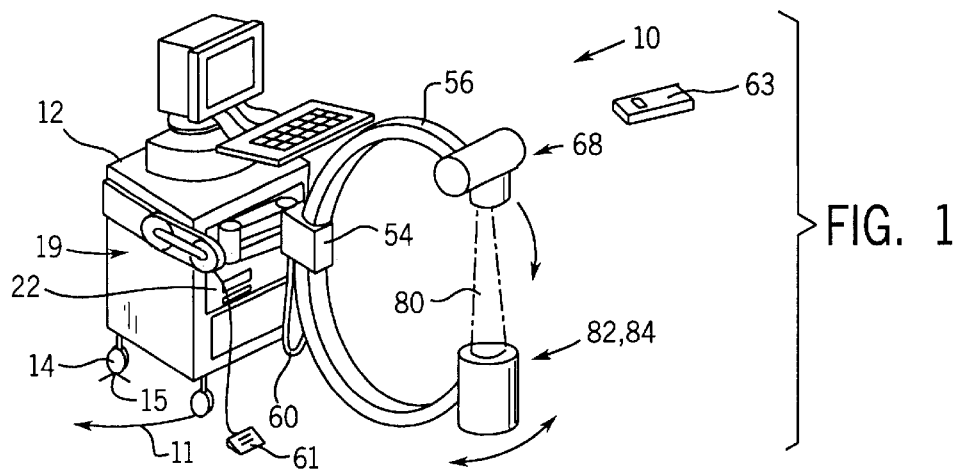
FIG. 1 is a perspective view of the fluoroscopy machine suitable for use with the present invention showing a C-arm supporting an image intensifier/video camera and x-ray tube in opposition for rotation in a vertical plane, the C-arm held along a mid-line of a cart by an articulated arm attached to the side of the cart.

Referring now to FIG. 1, an x-ray machine 10 per the present invention includes a generally box-shaped cart 12 having castors 14 extending downward from its four lower corners. The castors 14 have wheels rotating about a generally horizontal axis, and swiveling about a generally vertical axis passing along the edges of the cart 12. Castors 14, as are understood in the art, may be locked against swiveling and/or against rotation.

With one castor 14 locked and the others free to rotate and swivel, a pivot point 15 for the cart 12 is established with respect to the floor such as may be used as a first positioning axis 11 for the x-ray machine 10.

Positioned on the top of the cart 12 is a turntable 16 holding a video monitor 18 and attached keyboard 20 for swiveling about a vertical axis for convenience of the user. The video monitor 18 and the keyboard 20 may swivel separately so that one operator may view the video monitor 18 while a second operates the keyboard 20.

The video monitor 18 and the keyboard 20 allow for control of a computer 22 contained in a shelf on the cart 12 open from the front of the cart 12. The computer 22 may include a general microprocessor-type processor 23 and a specialized image processor 27 for particular functions as will be described. The computer 22 further includes a number of interface boards allowing it to provide control signals to various components of the x-ray machine 10 as will be described and to receive x-ray image data. In addition, the computer 22 receives signals from a foot switch 61 that is used to activate the x-ray system for a brief exposure. Control of the computer 22 may also be accomplished through a remote control wand 63 of a type known in the art.

Figure 2:
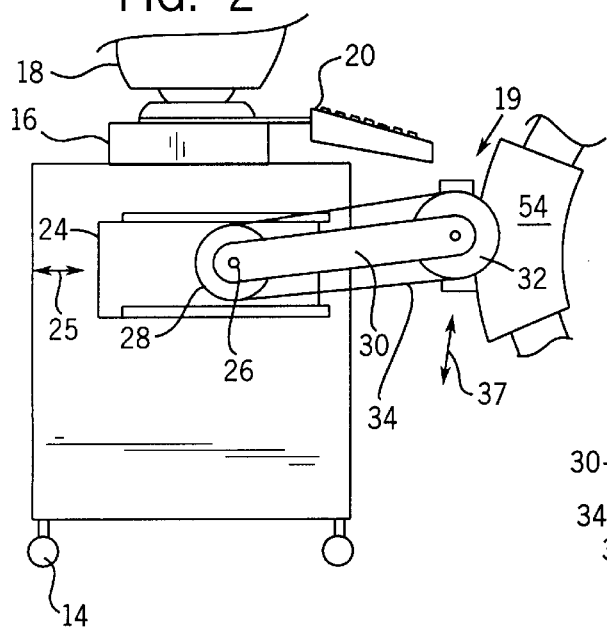
FIG. 2 is a side view in elevation of the cart of FIG. 1 showing a slide attaching the articulated arm to the side of the cart and showing a four-bar linkage motion of the arm for elevation of the C-arm.

Referring now also to FIG. 2, attached to the right side of the cart 12 is a horizontal slide 24 positioned to provide an attachment point 26 for an articulated arm 19 supporting a substantially circular C-arm 56, which in turn holds an x-ray tube 68 and an image intensifier 82 and camera 84, in opposition, and facing each other as will be described below. The function of the x-ray tube, the image intensifier and the camera are well known in the prior art in the use of mobile C-arm type x-ray devices used for image display and are described in U.S. Pat. No. 4,797,907 hereby incorporated by reference as part of the prior art. The C-arm may be mass balanced, that is to say its weight may be distributed to reduce its tendency to rotate through collar 54 so that minimal frictional pressure may be used to prevent it from moving.

The articulated arm 19 may be slid horizontally toward the front of the cart 12 to provide a second positioning axis 25 of the x-ray machine 10. A first pulley 28 is rotatively fixed in a vertical plane, attached to the portion of the slide 24 that may move with respect to the cart 12, and is pivotally attached to a rigid arm 30 extending toward the front of the cart 12. The other end of the rigid arm 30 supporting a second pulley 32 is also mounted to swivel with respect to arm 30. A belt 34 wraps around a portion of the circumference of each of pulleys 28 and 32 and is affixed at one point along that circumference to each of the pulleys 28 and 32 so that pivoting motion of the arm 30 about the center point 26 of pulley 28 causes rotation of pulley 32 so that it maintains a fixed rotational orientation with respect to the cart 12 as pulley 32 and hence C-arm 56 is moved up and down along a third axis 37. The linkage, so created, is a variation of the "four bar linkage" well known in the art.

Helical tension springs (not shown for clarity) balance the pulley 32 in rotative equilibrium about point 26 against the weight of the articulated arm 19, C-arm 56, and other devices attached to the arm 19.

Attached to pulley 32 is a third pulley 36 extending in a generally horizontal plane perpendicular to the plane of pulley 32. The third pulley 32 is attached pivotally to a second rigid arm 40 which at its other end holds another pulley 38 positioned approximately at the midline 41 of the cart 12. The midline 41 symmetrically divides the left and right sides of the cart 12.

Portions of the circumference of pulleys 36 and 38 are also connected together by a belt 44 so as to form a second four bar linkage allowing pulley 38 to move toward and away from the cart 12, along a fourth positioning axis 45, with pulley 38 and C-arm 56 maintaining their rotational orientation with respect to cart 12.

Figure 4:
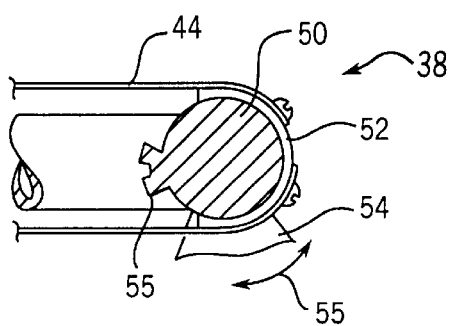
FIG. 4 is a detail fragmentary view of an outer pivot of the articulated arm attached to the C-arm such as allows limited pivoting of a plane of rotation of the C-arm about a vertical axis.

Referring now to FIG. 4, pulley 38 includes a center shaft member 50 having a coaxial outer collar 52 to which belt 44 is attached. A stop 55 attached to the shaft 50 limits the motion of the collar 52 in rotation with respect to the shaft 50 to approximately 26 degrees. Frictional forces between shaft 50 and collar 52 cause shaft 50 to maintain its rotational orientation with respect to collar 52 and hence with respect to pulley 36 until sufficient force is exerted on shaft 50 to displace it with respect to collar 52. Thus pressure on the C-arm 56 can provide some pivoting motion of the C-arm about the axis of the pulley along the fifth positional axis 55.

Figure 3:
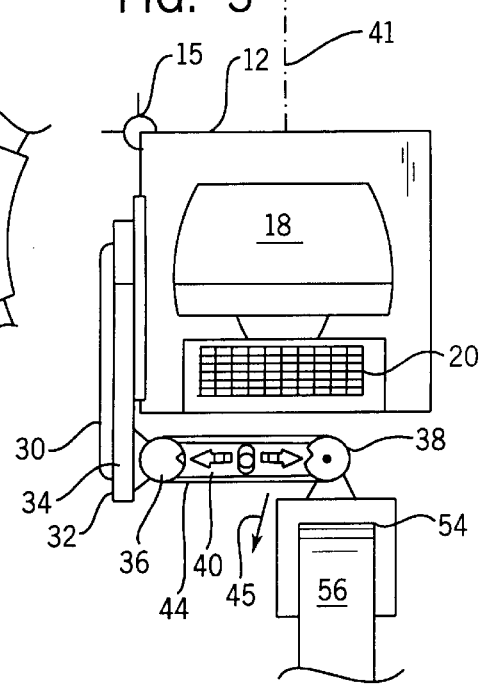
FIG. 3 is a top view of the C-arm system of FIG. 1 with the articulated arm in partial phantom showing the four-bar linkage of the arm for extending the C-arm toward and away from the cart.

Referring now to FIGS. 1, 3 and 4, attached to the shaft 50 is a C-arm collar 52 supporting the arcuate C-arm 56 curving through an approximately 180 degree arc in a vertical plane substantially aligned with the midline 41 of the cart 12 as has been mentioned. The shaft 50 may connect to collar 52 so that the latter may swivel in about a horizontal axis bisecting the circle of the C-arm 56. This axis may be aligned with the center of mass of the C-arm 56 so that there is not a self-righting tendency of the C-arm or the axis may be placed above the axis of the C-arm so as to provide for a beneficial self righting action. This motion is orthogonal to that provided by motion of shaft 50 and may augment that provided by the castors 14. Techniques of balancing the C-arm in its various rotational modes, when this is desired, is taught by U.S. Pat. No. 5.038,371 to Janssen issued Aug. 6th, 1991 and hereby incorporated by reference as exemplifying the known prior art understood to all those of ordinary skill in the art.

As described above, motion of the collar 52 may be had in a vertical manner by means of the parallelogram linkage formed by pulleys 28 and 32 of the articulated arm 19 as shown in FIG. 2. Forward and backward motion away from and toward the cart 12 may be had by the second four bar linkage formed from pulleys 36 and 38. A slight pivoting of the C-arm 56 about a vertical axis slightly to the rear of the collar 52 and concentric with the axis of pulley 38 may be had by means of the rotation between collar 52 and 50 of FIG. 4. Greater rotation of the C-arm about the vertical axis passing through pivot point 15 may be had by rotation of the cart about one of its stationary castors 14. Thus, considerable flexibility in positioning the C-arm may be had.

Figure 5:
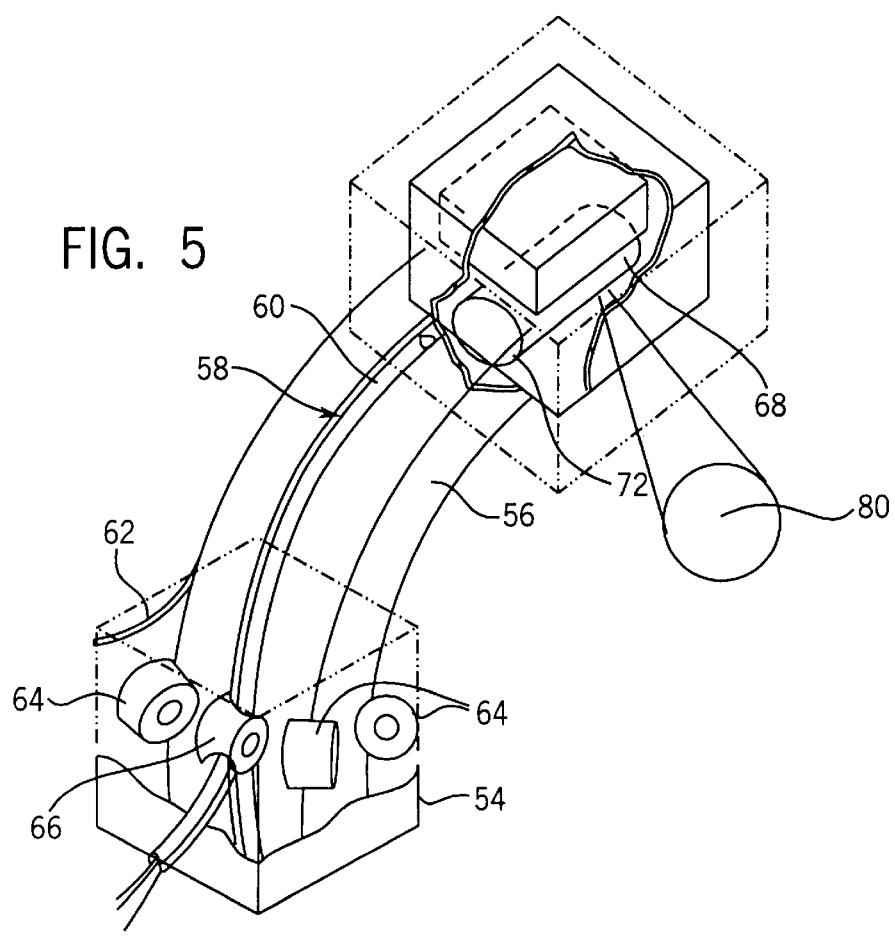
FIG. 5 is a detail view of the C-arm of FIG. 1 and the attached x-ray tube assembly showing the electrical cabling providing power to an x-ray tube power supply fitting into a groove in the C-arm and showing an abutment of the anode of the x-ray tube against the metal casting of the C-arm for heat sinking purposes.

Referring now to FIG. 5, the C-arm 56 is an aluminum casting having formed along its outer circumference a channel 58 into which a cable 60 may be run as will be described. C-arm 56 has a generally rectangular cross-section taken along a line of radius of the C-arm arc. Each corner of that rectangular cross-section holds a hardened steel wire 62 to provide a contact point for corner bearings 64 within the collar 52. The corner bearings 64 support the C-arm 56 but allow movement of the C-arm 56 along its arc through the collar 52.

A cable guide pulley 66 positioned over the channel 58 and having a concave circumference feeds the cable 60 into the channel 58 as the C-arm moves preventing tangling of the cable 60 or its exposure at the upper edge of the C-arm 56 when the C-arm 56 is rotated. The excess length of cable 60 loops out beneath the collar 52.

X-Ray Tube Cooling

Figure 6:
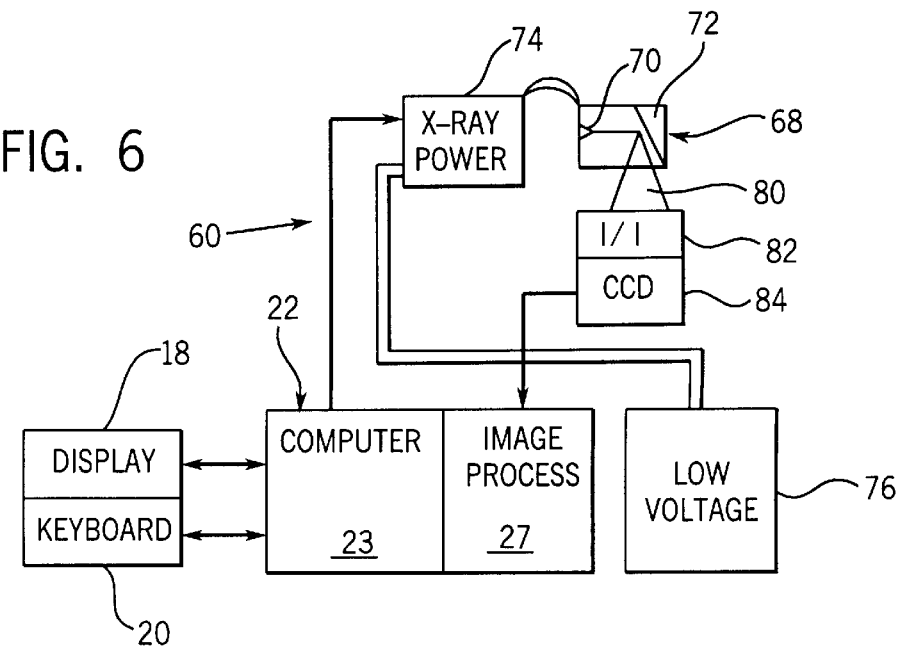
FIG. 6 is a schematic block diagram of the fluoroscopy machine of FIG. 1 showing the path of control of a remote x-ray tube power supply by a microprocessor and the receipt of data from the image intensifier/video camera by the microprocessor for image processing.

Referring now to FIGS. 5 and 6, the C-arm supports at one end a generally cylindrical x-ray tube 68 having a cathode 70 emitting a stream of electrons against a fixed anode 72. The conversion efficiencies of x-ray tubes are such that the anode 72 can become quite hot and typically requires cooling. In the present invention, the anode 72 is positioned to be bolted against the aluminum casting of the C-arm 56 thereby dissipating its heat into a large conductive metal structure of the C-arm 56.

The x-ray tube 68 is connected to an x-ray tube power supply 74 which separately controls the current and voltage to the x-ray tube 68 based on signals received from the computer 22 as will be described. The control signals to the x-ray tube power supply 74 are encoded on a fiber optic within the cable 60 to be noise immune. Low voltage conductors are also contained within cable 60 to provide power to the x-ray tube power supply 74 from a low voltage power supply 76 positioned on the cart 12.

During operation, an x-ray beam 80 emitted from the x-ray tube 68 passes through a patient (not shown) and is received by an image intensifier 82 and recorded by a charge couple device ("CCD") camera 84 such as is well known in the art. The camera provides digital radiation values to the computer 22 inversely proportional to the x-ray absorption of the imaged object for processing as will be described below. Each radiation value is dependent on the intensity of x-ray radiation received at a specific point on the imaging surface of the image intensifier 82.

Image Noise Reduction

Referring now to FIGS. 6 and 7, the data collected by the CCD camera 84 may be used to provide an image 86 displayed on video monitor 18. As will be described in more detail below, the CCD camera receiving a light image from the image intensifier 82 at a variety of points, provides data to the computer which maps the data from the CCD camera 84 to a pixel 88 in the image 86. For convenience, the data from the CCD camera 84 will also be termed radiation data reflecting the fact that there is not necessarily a one-to-one correspondence between data detected by the CCD camera 84 and pixels 88 displayed on the video monitor 18.

The CCD camera 84 provides a complete set of radiation data for an entire image 86 (a frame) periodically once every "frame interval" so that real-time image of a patient placed within the x-ray beam 80 may be obtained. Typical frame rates are in the order of thirty frames per second or thirty complete readouts of the CCD detector area to the computer 22 each second.

Each frame of data is stored in the memory of the computer 22 and held until after complete storage of the next frame of data. The memory of the computer 22 also holds an average frame of data which represents an historical averaging of frames of data as will now be described and which is normally used to generate the image on the video monitor 18.

In a typical image 86, there will be some stationary object 90 such as bone and some moving object 92 such as a surgical instrument such as a catheter. In a second image 86' taken one frame after the image 86, the bone 90 remains in the same place relative to the edge of the image 86 and 86', however the surgical instrument 92 has moved. Accordingly, some pixels 88' show no appreciable change between images 86 and 86', whereas some other pixels 88" show a significant change between images 86 and images 86'.

Figure 9:
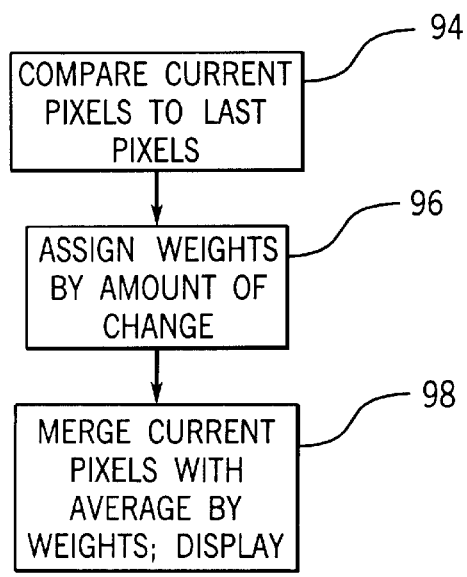
FIG. 9 is a flow chart of a method of the present invention providing differently weighted noise reduction to different areas of the image based on motion in the areas of the image.

Referring now to FIG. 9, as data arrives at the computer 22, the computer 22 executes a stored program to compare current pixels of the image 86' to the last pixels obtained from image 86 as indicated by process block 94. This comparison is on a pixel by pixel basis with only corresponding pixels in the images 86 and 86' compared. The difference between the values of the pixels 88, reflecting a difference in the amount of x-ray flux received at the CCD camera 84, is mapped to a weight between zero and one, with greater difference between pixels 88 in these two images corresponding to larger values of this weight w. This mapping to the weighting is shown at process block 96.

Thus pixels 88", whose value changes almost by the entire range of pixel values between images 86 and 86', receive a weighting of "one" whereas pixels 88' which have no change between images 86 and 86' receive a value of zero. The majority of pixels 88 being neither unchanged nor radically changed will receive a value somewhere between zero and one.

Generally, because the amount of x-ray fluence in the beam 80 is maintained at a low level to reduce the dose to the patient, the images 86 and 86' will have appreciable noise represented as a speckling in the images 86 and 86'. This noise, being of random character, may be reduced by averaging data for each pixel 88 over a number of frames of acquisition effectively increasing the amount of x-ray contributing to the image of that pixel.

Nevertheless, this averaging process tends to obscure motion such as exhibited by the surgical instrument 92. Accordingly, the present invention develops an average image combining the values of the pixels acquired in each frame 86, 86' in which those pixels in the current image 86' which exhibit very little change between images 86 and 86' contribute equally to the average image, but those pixels in the current image 86' that exhibit a great degree of change between images 86 and 86' are given a substantially greater weight in the average image. In this process, a compromise is reached between using historical data to reduce noise and using current data so that the image accurately reflects changes. Specifically, the value of each pixel displayed in the image is computed as follows.

$$P_i = (1-w)P_{i-1} + wP_{i,t} \quad (1)$$

where $P_{i-1}$ is a pixel in the previous average image, w is the weighting factor described above and $P_{i,t}$ is the current data obtained from the CCD camera 84. This effective merger of the new data and the old data keyed to the change in the data is shown at process block 98.

Image Intensifier Distortion

Figure 10:
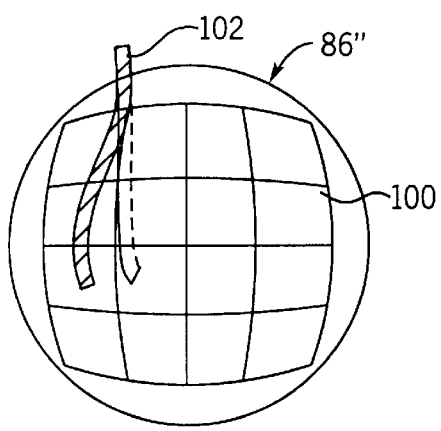
FIG. 10 is a figure similar to that of FIG. 7 showing an image of a rectilinear grid as affected by pincushion distortion in the image intensifier and video camera optics such as may provide a confusing image of a surgical tool being manipulated in real-time.

Referring now to FIG. 10, an image 86" of a rectilinear grid 100 positioned in the x-ray beam 80 will appear to have a barrel or pincushion shape caused by distortion of the image intensifier 82 and the optics of the CCD camera 84. During a real-time use of the image 86" by a physician, this distortion may cause confusion by the physician controlling a tool 102. For example, tool 102 may be a straight wire shown by the dotted line, but may display an image 86' as a curved wire whose curvature changes depending on the position of the tool 102 within the image 86. This distortion thus may provide an obstacle to a physician attempting to accurately place the tool 102 with respect to an object within the image 86'.

Figure 11:
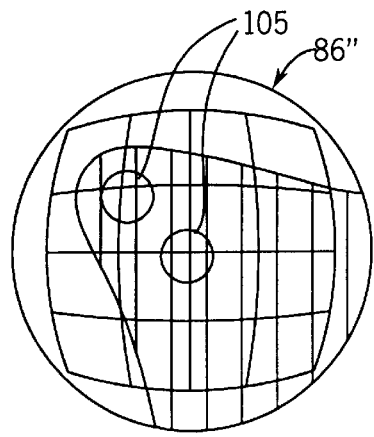
FIG. 11 is a figure similar to FIG. 10 showing equal areas of the image that encompass different areas of the imaged object, such variation as may affect quantitative bone density readings.

Referring now to FIG. 11, the distortion of image 86" also means that two equal area regions of interest 105 (equal in area with respect to the image) do not encompass equal areas of the x-ray beam 80 received by the image intensifier 82. Accordingly, if the data from the CCD camera 84 is used for quantitative purposes, for example to deduce bone density, this distortion will cause an erroneous variation in bone density unrelated to the object being measured.

Accordingly, the present inventors have adopted a real-time digital re-mapping of radiation data from the CCD camera 84 to the image 86 to correct for any pincushion-type distortion. This remapping requires the imaging of the rectilinear grid 100 and an interpolation of the position of the radiation data received from the CCD camera 84 to new locations on the image 86" according to that test image. By using digital processing techniques in a dedicated image processor 27, this remapping may be done on a real-time basis with good accuracy.

Referring to FIG. 19, there are two types of distortion, isotropic and anisotropic. Isotropic distortion is rotationally symmetric (e.g. like barrel and pin cushion distortion). Anisotropic distortion is not rotationally symmetric. Both types of distortion and rotation are so-called third order aberrations which can be written in the form:

$$Dx = r^2(Du - dv) \quad (2)$$

$$Dy = r^2(Dv + du) \quad (3)$$

where Dx and Dy are pixel shifts due to distortion; r is the distance from the correct position to the optical axis and D and d are distortion coefficients which are constant and u and v are correct pixel positions.

Referring also FIG. 2, received image 86 may exhibit pin cushion distortion evident if an image 86 of the rectilinear grid 100 is made. The distortion is caused by the pixel shifts described above.

Equations 1 and 2 may be rewritten as third order two-dimensional polynomials, the case for equation (1) following:

$$x = (a_x + e_x v + i_x v^2 + m_x v^3) + (b_x + f_x v + j_x v^2 + n_x v^3)u + (c_x + g_x v + k_x v^2 + o_x v^3)u^2 + (d_x + h_x v + l_x v^2 + p_x v^3)u^3 \quad (4)$$

In these polynomials, $a_x$ and $a_y$ govern the x and y translation of the image, $e_x$ and $b_y$ take care of scaling the output image, while $e_y$ and $b_x$ enable the output image to rotate. The remaining higher order terms generate perspective, sheer and higher order distortion transformations as will be understood to those of ordinary skill in the art. Thirty-two parameters are required for the two, third order polynomials. These parameters may be extracted by a program executed by the computer in an off-line (non-imaging) mode after imaging the known grid 100 and comparing the distorted image of the grid 100 to the known grid 100 to deduce the degrees of distortion.

Referring now to FIG. 19 in a first step of the correction process, the grid 100 is imaged as indicated by process block 160 to determine the exact type of distortion present and to obtain values for the coefficients a through p of the above referenced polynomial equations.

At process block 166, these parameters may be input to the computer 22 and used at a transformation of received image 86 into image data 164 as indicated by process block 168. For rotation of the image 164, new parameters of the polynomials may be entered by means of hand-held remote control wand 63 shown in FIG. 1.

The transformation process generally requires a determination of the pixel shift for each radiation pixel 163 of the input image 86 which in turn requires an evaluation of the polynomials whose coefficients have been input. A number of techniques are known to evaluate such polynomials including a forward differencing technique or other techniques known in the art. These transformations provide values of u and v for an image pixel 170 corresponding to a particular radiation pixel 163.

After the transformation of process block 168, the u, v locations of the radiation pixels will not necessarily be centered at a pixel location defined by the hardware of the video monitor 18 which usually spaces pixels 170 at equal distances along a Cartesian axis. Accordingly, the transformed pixels must be interpolated to actual pixel locations as indicated by process block 172.

A number of interpolation techniques are well known including bilateral and closest neighbor interpolation, however in the preferred embodiment, a high resolution cubic spline function is used. A given value of an interpolated pixel 170 ($P_{int}$) is deduced from a 4×4 block of transform pixels ($P_{i,j}$) in which it is centered as follows:

$$P_{int} = f(n-2)X_1 + f(n-1)X_2 + f(n)X_3 + f(n+1)X_4 \quad (5)$$

where:

$$X_i = f(m-2)P_{i,1} + f(m-1)P_{i,2} + f(m)P_{i,3} + f(m+1)P_{i,4} \quad (6)$$

where:

$$f(x) = (a+2)x^3 + -(a+3)x^2 + 1 \text{ for } x \in [0,1];$$

$$f(x) = ax^3 + -5ax^2 + 8ax - 4a \text{ for } x \in [1,2]; \quad (7)$$

f(x) is symmetrical about zero. In the preferred embodiment a=−0.5 and where m and n are fractions indicating the displacement of the neighboring pixels $P_{i,j}$ with respect to $P_{int}$ in the x and y directions, respectively.

At process block 180, the transformed and interpolated image is displayed.

Noise Equalization

Figure 12:
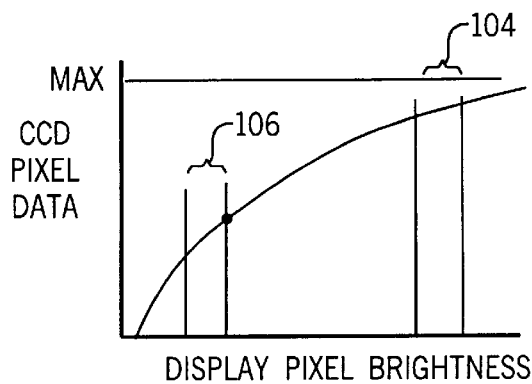
FIG. 12 is a plot of raw image data from the image intensifier/video camera as is translated into pixel brightness in the images of FIGS. 7, 8, 10, and 11 by the microprocessor of FIG. 6 according to a non-linear mapping process such as provides noise equilibrium in the images and maximum dynamic range for clinical data.

Referring now to FIG. 12, the radiation data from the CCD camera 84 are mapped to the brightness of the pixels of the image 86 according to a second transformation. In the preferred embodiment, this mapping between CCD radiation data and image pixel brightness follows a nonlinear curve 103 based on the hyperbolic tangent and being asymptotically increasing to the maximum CCD pixel value. This curve is selected from a number of possibilities so that equally wide bands of image pixel brightness 104 and 106 have equal amounts of image noise. The curve 103 is further positioned to provide the maximum contrast between clinically significant tissues in the image.

Exposure Control

The noise in the image 86 is further reduced by controlling the fluence of the x-ray beam 80 as a function of the density of tissue of the patient within the beam 80. This density is deduced from the image 86 itself produced by the CCD camera 84. In response to the image data, a control signal is sent via the fiber optic strand within the cable 60 to the x-ray tube power supply 74 positioned adjacent to the x-ray tube 68 (shown in FIG. 5). By positioning the x-ray tube power supply 74 near the x-ray tube 68, extremely rapid changes in the power supplied to the x-ray tube 68 may be obtained. Distributed capacitances along high tension cables connecting the x-ray tube 68 to a stationary x-ray tube power supply are thus avoided in favor of low voltage cable 60, and the shielding and inflexibility problems with such high tension cables are also avoided.

Automatic Technique Control

Figure 13:
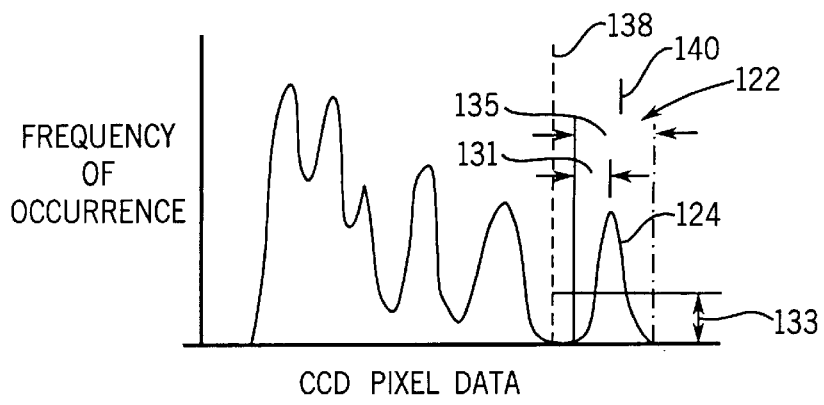
FIG. 13 is a histogram plotting values of data from the image intensifier/video camera versus the frequency of occurrence of data values showing an isolated Gaussian distribution at the right most side representing unattenuated x-ray values.
Figure 14:
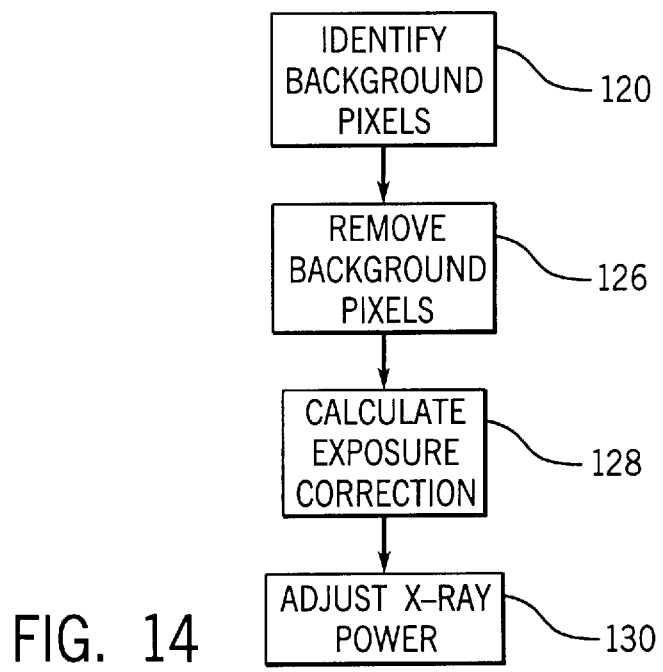
FIG. 14 is a flowchart describing the steps taken by the programmed microprocessor of FIG. 6 to identify background pixels and remove them from a calculation of exposure rate used for controlling the remote x-ray tube power supply of FIG. 6.
Figure 20:
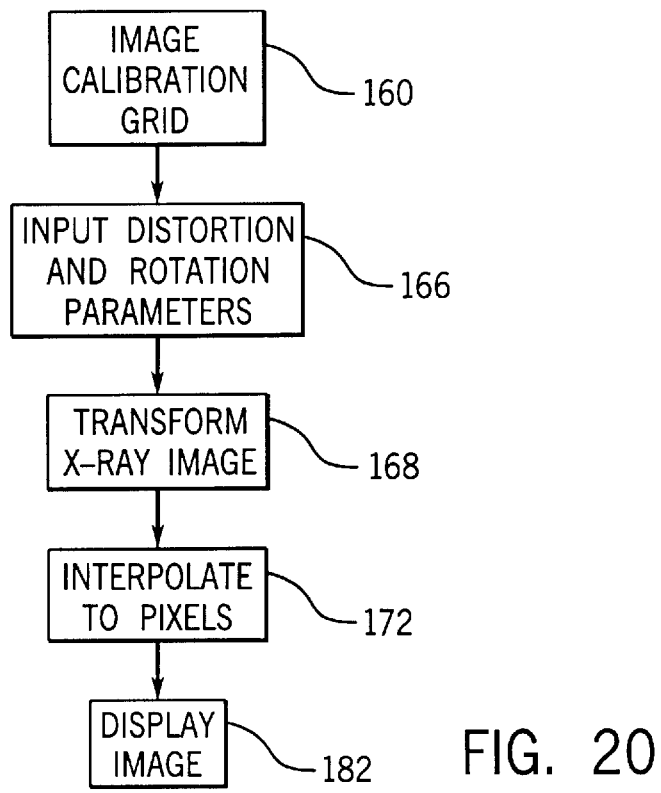
FIG. 20 is a flow chart of the steps performed by the computer in correcting and transforming the image of FIGS. 11 and 19.

Referring now to FIGS. 13 and 14, a determination of the proper control signal to send to the x-ray tube power supply 74 begins by analyzing the image data 86 as shown in process block 120. The goal is to provide for proper exposure of an arbitrary object placed within the x-ray beam 80 even if it does not fill the field of view of the CCD camera 84. For this reason, it is necessary to eliminate consideration of the data from the CCD camera 84 that form pixels in the image corresponding to x-rays that bypass the imaged object and are unattenuated ("background pixels"). These background pixels may be arbitrarily distributed in the image 86 and therefore, this identification process identifies these pixels based on their value. To do this, the computer 22 collects the values of the pixels from the CCD camera 84 in a histogram 122 where the pixels are binned according to their values to create a multiple peaked plot. The horizontal axis of the histogram 122 may for example be from 0 to 255 representing 8 bits of gray scale radiation data and the vertical axis may be a number of pixels having a particular value.

If there is a histogram value at horizontal value 255, and the maximum gray scale exposure recorded, the entire area of the histogram 122 is assumed to represent the imaged object only (no background pixels). Such a situation represents an image of raw radiation only or a high dose image of a thin object with possible clipping. In assuming that the whole histogram 122 may be used to calculate technique without removal of background pixels, a reduced exposure rate will result as will be understood from the following description and the peak classification process, to now be described, is skipped.

Otherwise, if there are no pixels with the maximum value of 225, the present invention identifies one peak 124 in the histogram 122 as background pixels indicated by process block 120 in FIG. 14. In identifying this peak 124, the computer 22 examines the histogram 122 from the brightest pixels (rightmost) to the darkest pixels (leftmost) assuming that the brightest pixels are more likely to be the unattenuated background pixels. The process block 120 uses several predetermined user settings as will be described below to correctly identify the peak 124.

Once the peak 124 has been identified, the pixels associated with that peak are removed per process block 126 by thresholding or subtraction. In the thresholding process, pixels above a threshold value 138 below the peak 124 are considered to be background pixels and are omitted from an exposure rate calculation. In the subtraction method, the peak 124 itself is used as a template to identify pixels which will be removed.

At process block 128, an exposure rate is calculated based on the values of the pixels in the remaining histogram data and at process block 130, an amperage and voltage value are transmitted via the cable 60 to the x-ray tube power supply and used to change the power to the x-ray tube. Generally, if the exposure rate is above a predetermined value, the amperage and voltage are adjusted to cut the x-ray emission from the x-ray tube, whereas if the exposure rate is below the predetermined value, the amperage and voltage are adjusted to boost the exposure rate to the predetermined value.

Figure 15:
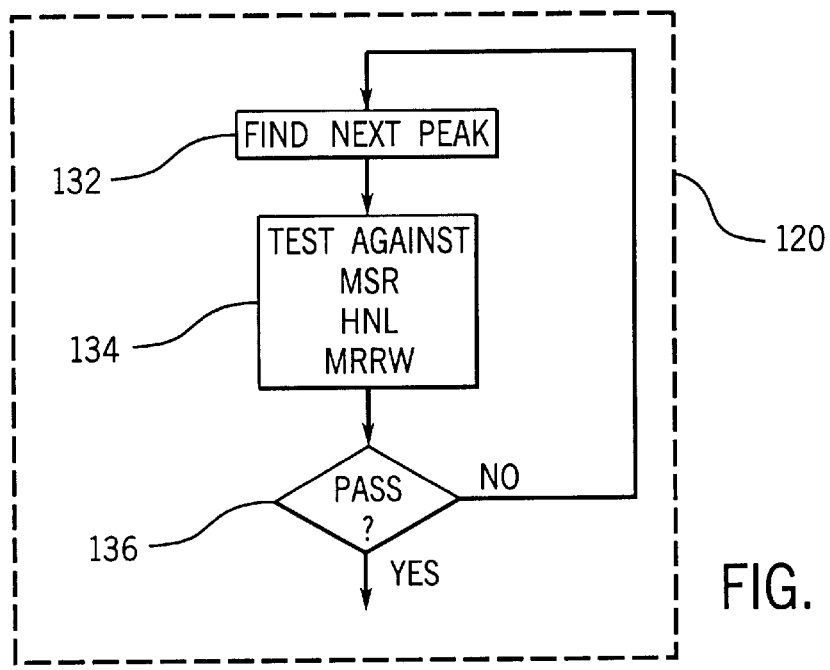
FIG. 15 is a detailed block diagram of the first block of the flow chart of FIG. 14.

Referring now to FIGS. 13, 14 and 15, the process of identifying background pixels will be explained in more detail. Process block 120 includes as a first step, an identification of a right most peak 124 in the histogram 122 (shown in FIG. 13) as indicated by subprocess block 132.

At succeeding subprocess block 134, this right most peak 124 is compared against three empirically derived parameters indicated in the following Table 1:

TABLE 1

| Minimum Slope Range (MSR) | Minimum necessary pixel range for which the slope of the peak must be monitonically increasing. |
|---|---|
| Histogram Noise Level (HNL) | Minimum height of the maximum value of the peak. |
| Maximum Raw Radiation Width (MRRW) | Maximum width of the detected peak with respect to the width of the entire histogram. |

Specifically at subprocess block 134, each identified peak 124 is tested against the three parameters indicated in Table 1. In the description in Table 1, "width" refers to the horizontal axis of the histogram 122 and hence a range of pixel values, whereas "height" refers to a frequency of occurrence for pixels within that range, i.e., the vertical axis of the histogram 122.

These first two tests, MSR and HNL, are intended to prevent noise peaks and peaks caused by bad imaging elements in the CCD camera 84 or quantization of the video signal in the A to D conversion from being interpreted as background pixels.

Peaks 124 with a suitable stretch of monotonically increasing slope 131 (shown in FIG. 13) according to the MSR value and that surpass the histogram noise level HNL 133 are evaluated against the MRRW parameter. This third evaluation compares the width 135 of the histogram 122 against the width of the entire histogram 122. The MRRW value is intended to detect situations where the imaged object completely fills the imaging field and hence there are no unattenuated x-ray beams or background pixels being detected. A valid peak 124 will normally have a width 135 more than 33% of the total width of the histogram 122.

At decision block 136 if the peak 124 passes the above tests, the program proceeds to process block 126 as indicated in FIG. 14. Otherwise, the program branches back to process block 132 and the next peak to the left is examined against the tests of process block 134 until a passing peak is found or no peak is found. If no peak is found, it is assumed that there are no background pixels and a raw exposure value is calculated from all pixels as described above.

Assuming that a peak 124 passes the tests of Table 1, then at process block 126 background pixels identified by the peak 124 selected at process block 120 are eliminated.

Figure 16:
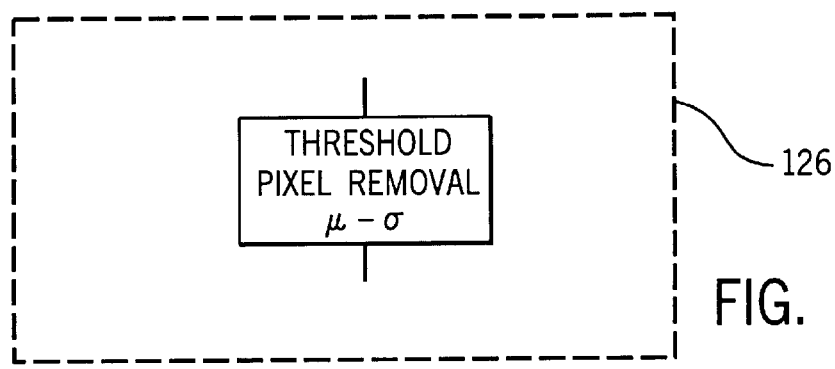
FIG. 16 is a first embodiment of the second block of the flow chart of FIG. 14.
Figure 17:
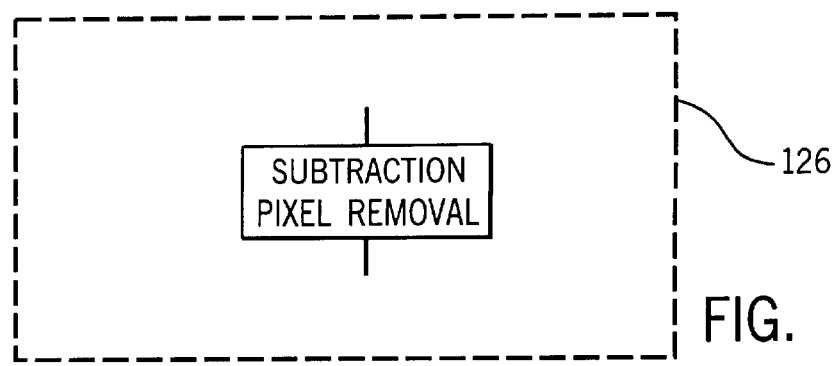
FIG. 17 is a second embodiment of the second block of the flow chart of FIG. 14.

In a first method of eliminating background pixels indicated at FIG. 16, a magnitude threshold 138 within the histogram 122 is identified. Pixels having values above this threshold will be ignored for the purpose of selecting an exposure technique. The threshold 138 is established by identifying the center 140 of the peak 124 (its maximum value) and subtracting from the value of the center a value s being the distance between the start of the peak 124 as one moves leftward and the maximum 140. The area under the histogram 122 for values lower than the threshold 138 is computed to deduce a raw exposure value which will be used as described below.

In a second embodiment, the shape of the histogram peak 124 from the start of the peak as one moves leftward to its maximum 140 is reflected about a vertical line passing through the maximum 140 and subtracted from the histogram peak 124 to the left of the vertical line. This approach assumes that the peak 124 of the background pixels is symmetrical and thus this method better accommodates some overlap between the object pixels and the background pixels in the histogram 122. Again, the remaining pixels of the histogram 122 are summed (by integration of the area under the histogram 122 minus the area of the peak 124 as generated by the reflection) to provide a raw exposure value.

Figure 18:
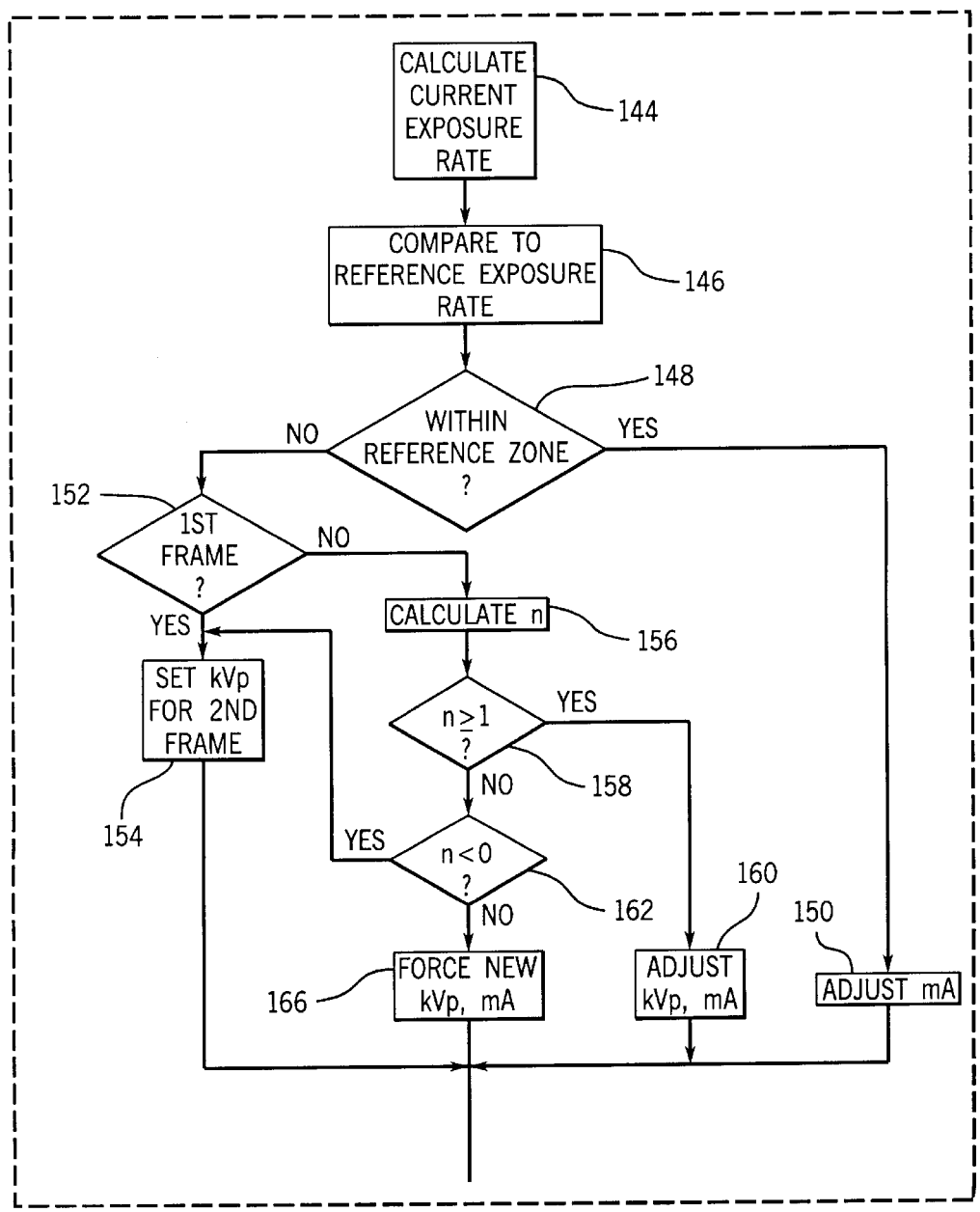
FIG. 18 is a detailed flow chart of the third block of the flow chart of FIG. 14.

Referring now to FIG. 18, the raw exposure value is transformed by the known transfer characteristics of the CCD camera (relating actual x-ray dose to pixel value) to produce a calculated current exposure rate as indicated at process block 144.

Referring to process block 146, the current exposure rate is next compared to a reference exposure rate, in the preferred embodiment being 1.0 mR per frame, however this value may be refined after further clinical testing. If at process block 148, the current exposure rate is within a "half fine-tune range" of the reference exposure rate, then the program proceeds to process block 150, a fine tuning process block, and the amperage provided to the x-ray tube are adjusted in accordance to the disparity between the amperage and reference exposure rate. That is, if the current exposure is greater than the reference exposure rate, the amperage to the x-ray tube is reduced. The new value of amperage is compared against a predetermined range of amperage values (maximum beam current and minimum beam current values) so that the amperage value may never vary outside of this range.

If at decision block 148, the current exposure rate is outside of the half fine tune range established at decision block 148, a more substantial adjustment process is undertaken. Generally, the exposure provided by an x-ray system will follow the following equation:

$$X \approx s \cdot mA \cdot kVp^n. \qquad (8)$$

where:
s is seconds,
mA is the amperage provided to the x-ray tube,
kVp is the voltage provided to the x-ray tube, and
n is a power factor dependent on the geometry of the machine and the particular kind of object being imaged.

Generally, the value of n will not be known in advance. Accordingly in the more substantial correction process, n is deduced by obtaining two different exposures for equal predetermined intervals with different kVp values so that the value of n may be deduced.

At decision block 152, it is determined whether a first or second reference exposure is to be obtained. If the first reference exposure was just obtained, the program proceeds to process block 154 and a new value of kVp is determined for a second exposure. In this case, the first exposure used will be that which was employed to produce the histogram 122 as previously described.

If the comparison of process block 148 indicated that the exposure rate was too high, a lower kVp value is selected;

and conversely, if the exposure at process block 148 indicated the exposure was too low, an increased value of kVp is provided. The new kVp value for the second exposure must be within a predetermined range of kVp values established by the user. Mathematically, the kVp value selected may be described as:

$$kVp_2 = kVp_1 + a(dkVp) \qquad (9)$$

where a is a step factor and dkVp is a minimum practical change in tube voltage.

Two preferred means of selecting may be used: one providing linear and one providing logarithmic scaling. Such scaling techniques are well understood to those of ordinary skill in the art.

If at decision block 152, a second frame has already been taken with the new voltage value, then the program proceeds to process block 156 and the value of n in equation (9) is calculated. If the value of amperage is held constant between the first and second frame, the value of n may be determined according to the following equation:

$$n = \log \frac{X_2}{X_1} \bigg/ \log \frac{kVp_2}{kVp_1} \qquad (10)$$

where $X_1$ and $X_2$ are the measured exposure rates at the first and second frames, respectively and $kVp_1$ and $kVp_2$ are the two x-ray tube voltages during the first and second frames.

At process block 158, this value of 'n' is checked against threshold values intended to detect whether an erroneous value of n has been produced as a result of 'clipping' in the radiation data used to calculate exposure. As is understood in the art, clipping occurs when an increased dose of an element of the CCD camera produces no increase in the camera's output.

At decision block 158, if the value of n calculated at process block 156 is greater than or equal to one, it is assumed to be valid and the program proceeds to process block 160 where kVp and mA are adjusted by setting mA equal to a maximum reference value and calculating kVp according to the following equation:

$$kVp_{new} = kVp_2 \left( \frac{X_{ref} mA_2}{X_2 mA_{ref}} \right) 1/n \qquad (11)$$

where $kVp_{new}$ and $mA_{new}$ are the settings for the next frame to be shot.

If the resulting kVp value conflicts with the minimum system, kVp, kVp is set to the minimum system value and mA is calculated according to the following equation using the mA and kVp value of the second frame.

$$mA_{new} = mA_2 \frac{X_{ref}}{X_2} \left( \frac{kVp_2}{kVp_{min}} \right)^n \qquad (12)$$

If the value of n in decision block 158 is less than one, then at process block 162, n is tested to see if it is less than zero. This value of n is realized when the exposure rate of the second frame changes in the opposite direction of the tube voltage. This suggests a clipped histogram and therefore the program branches back to process block 154 to obtain a new second frame. This condition may also arrive from object motion between the first and second frame.

On the other hand, if at decision block 162, n is not less than zero (e.g. n is between zero and 1), the program proceeds to process block 166. Here it is assumed that because the sensitivity of the exposure rate on change in kVp is low, there may be some partial clipping. New values of kVp and mA are then computed and used with the previous second frame values to calculate a new n as follows. Generally, if kVp and mA are high, they are both lowered and if kVp and mA are low, they are both raised.

Scatter Reduction

Referring now to FIG. 1, the image produced by the present invention may be used for quantitative analysis including, for example, that of making a bone density measurement. It is known to make bone density analyses from x-ray images through the use of dual energy techniques in which the voltage across the x-ray tube is changed or a filter is periodically placed within the x-ray beam to change the spectrum of the x-ray energy between two images. The two images may be mathematically processed to yield information about different basis materials within the image object (e.g. bone and soft tissue). For these quantitative measurements, it is desirable to eliminate the effect of scatter.

Figure 23:
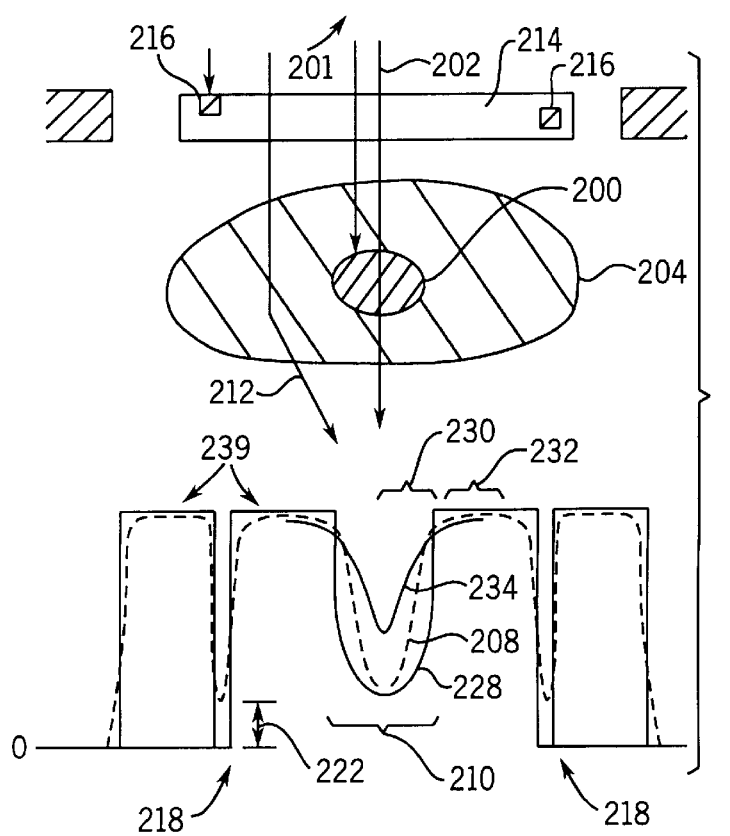
FIG. 23 is a cross-sectional view through the occluder of an imaged object of FIG. 21 along line 23—23, aligned with a graph depicting attenuation of x-rays as a function distance along the line of cross-section as well as theoretical attenuation without scatter and scatter components.

Referring now to FIG. 23 in imaging a patient's spine 200, for example, x-rays 202 are directed from an x-ray source 201 through the patient 199 to pass through soft tissue 204 surrounding a spine 200. Certain of the x-rays 202 are blocked by the spine 200 and others pass through the spine 200 to be recorded at the image intensifier 206. An attenuation image 208 measured by an image intensifier measures those x-rays passing through the patient 109.

A portion 210 of the attenuation image directly beneath the spine 200 records not only those x-rays 202 passing through the spine 200 and the soft tissue 204 above and below it, but also scattered x-rays 212 directed, for example, through soft tissue 204 to the side of the spine 200 but then scattered by the soft tissue to proceed at an angle to the portion 210 of the attenuation image 208 beneath the spine 200. Because the scattered x-rays 212 do not carry information about the attenuation of the spine 200, they are desirably removed from the image 208 prior to its use in quantitative measurement.

For this purpose, the present invention uses an occluder 214 being an x-ray transparent plate such as may be constructed of Plexiglas and incorporating into its body, a plurality of x-ray blocking lead pins 216. Preferably these pins are placed so as to project images 218 onto the image 208 received by the image intensifier 206 in positions outside an image 220 of the spine 200. Generally therefore, the pins 216 are placed at the periphery of the occluder 214. The pins 216 are sized so as to substantially block all direct x-rays from passing through them but so that their images 218 include a significant portion of scattered x-rays 212.

Figure 22:
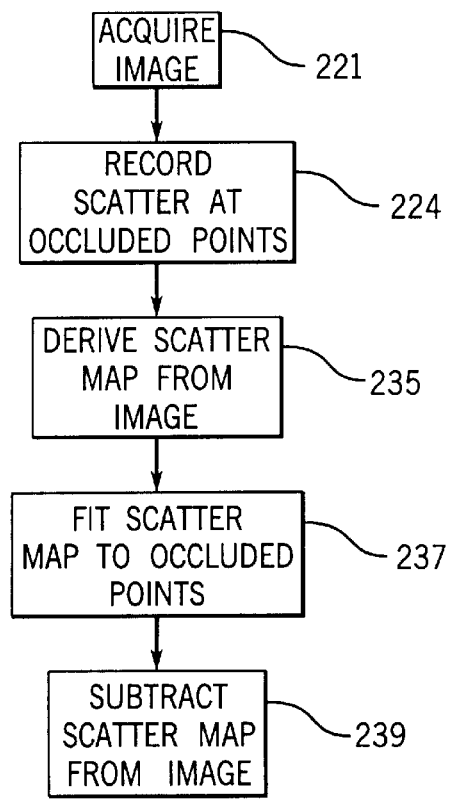
FIG. 22 is a flow chart of the steps of calculating and removing scatter using the occluder of FIG. 21.
Figure 21:
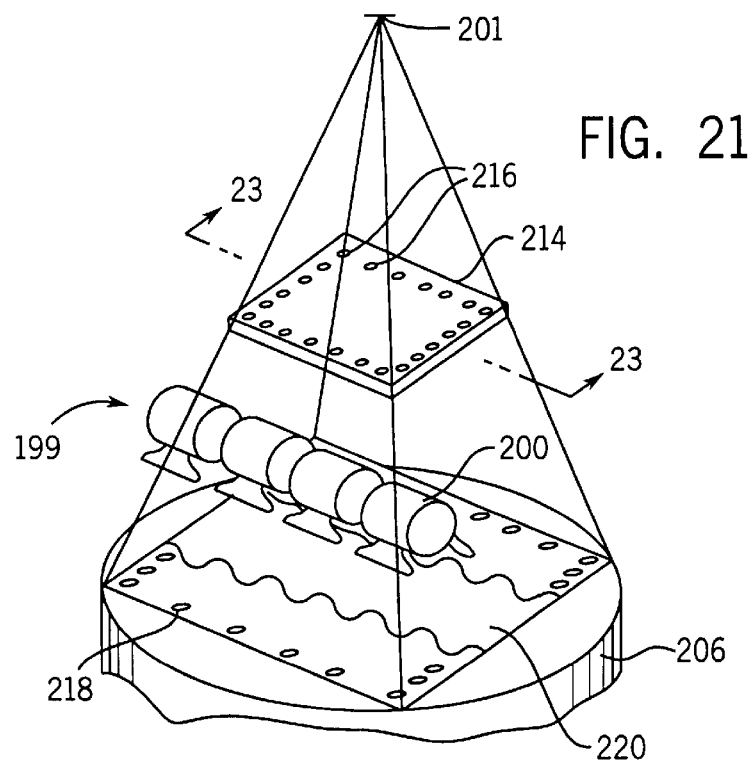
FIG. 21 is a perspective view of an occluder placed in an x-ray beam prior to an imaged object and used for calculating scatter.

Referring now to FIG. 22 at a first step of a scatter reduction operation with the occluder 214 of FIG. 21, an image is acquired of the imaged object, for example, the spine 200 and its surrounding soft tissue 204 (not shown in FIG. 21) including the images 218 of the pins 216. This acquisition is indicated by process block 221 of FIG. 22.

The pins 216 are held in predetermined locations with respect to the image 208 so that their images 218 may be readily and automatically identified. Preferably the pins 216 are placed at the interstices of a Cartesian grid, however, other regular patterns may be chosen. The image 208 may be corrected for pincushion type distortion, as described above, so that the locations of the pins 216 may be readily located in the image based on their known positions in the occluder 214.

At each pin image 218, a value 222 indicating the magnitude of the received x-rays, shown in FIG. 23, may be ascertained. This value 222 measures the scatter received in the vicinity of image 218 caused generally by the effect of the soft tissue 204 and possible secondary scatter effects in the image intensifier 206. Values 222 are recorded, as indicated by process block 224, for each pin image 218. From these values, a set of normalizing points are established.

The image 208 is then used to derive a scatter map. Referring to FIG. 23, generally the amount of scatter at a given point will be a function of how many x-ray photons are received at points adjacent to the given point. For example, comparing the image 208 to a theoretical scatterless image 228 generally in an attenuated region 230 of the image 208 (e.g., under the spine 200), scatter will increase the apparent value in the image 208 as a result of radiation from nearby low attenuation regions scattering into the high attenuation region 230. Conversely the apparent value at a low attenuation region 232 will be decreased because of the scatter into the high attenuation region.

A map of the scattered radiation may thus be modeled by "blurring" the image 208. This blurring can be accomplished by a low pass filtering of the image 208, i.e., convolving the image 208 with a convolution kernel having rectangular dimensions corresponding to the desired low pass frequency cut off. The effect is an averaging of the image 208 producing scatter map 234.

The image used to produce the scatter map 234 is an attenuation image 208 obtained from the patient 199 without the occluder 214 in place, or may be an image 208 including the images 218 of the pins 216 but with the latter images 218 removed based on knowledge of their location. This removal of images 218 may substitute values of the image 208 at points 239 on either side of the images 218. The process of driving the scatter map from the image is indicated by process block 235 of FIG. 24.

Next as indicated by process block 237, the scatter map 234 is fit to the normalizing points 222 previously determined at process block 224.

Referring to FIG. 24, the scatter map 234 is thus normalized so that the portions 238 of the scatter map 236 located near the places where the images 218 would fall are given values 222 as determined at process block 224. This involves a simple shifting up or down of the scatter map 236 and may employ a "least square" fit to shift the scatter map 236 to multiple values 222 obtained from each pin 216. As adjusted, the scatter map 236 is then subtracted from the image 208 to eliminate or reduce the scatter in that image as indicated by process block 239.

The effect of subtracting a low pass filtered or blurred image properly normalized to actual scatter is to sharpen up the image 208 but also to preserve its quantitative accuracy. Thus the present invention differs from prior art scatter reduction techniques in that it both addresses the variation in scatter across the image caused by attenuation of x-rays by the imaged object but also incorporates accurate measurements of scatter in certain portions of the image.

DENSITOMETER ADAPTER

Referring now to FIG. 25, a mobile fluoroscopy machine 310 suitable for use with the present invention is similar to that which has been described above with respect to FIG. 1 with exceptions that will be apparent from context.

The mobile fluoroscopy machine 310 includes a mobile cart 312 supporting a computer 314 and monitor and keyboard 317 for receiving and processing digital x-ray image data. The cart 312 supports on one side an articulating arm assembly 316 terminating in a rotatable C-arm 318. The C-arm supports, at the ends of the C, an image intensifier 320 and an x-ray source 322 opposed along an axis 324 so that the x-ray source 322 projects a cone-beam of x-ray radiation toward the image intensifier 320 along axis 324.

The articulating arm assembly 316 is connected to the C-arm 318 through one or more pivotal links 327 so that the axis 324 may be positioned to be horizontal approximately two feet above the floor to rest upon or be supported against the upper end of a supporting pedestal 326 or may be attached to the cart 312. Referring also to FIG. 26, the pedestal 326 includes a hemicylindrically concave cradle 328 at its upper surface to receive a lower portion of the cylindrical image intensifier 320 when the C-arm is so positioned to rest against the pedestal 326.

The pedestal 326 also provides on its upper surface a channel 330 extending across the axis 324 between the image intensifier 320 and the x-ray source 322 when the latter are positioned on the pedestal 326. The channel 330 may receive a limb positioner 332 such as may be adapted to support a patient's foot or arm across the axis 324 for densiometric measurement. The pedestal 326 may be weighted so as to provide a stable surface for support of the x-ray source 322 and image intensifier 320 and to provide adequate support for the patient's limb. The height of the pedestal 326 is selected to be suitable for either arm or foot imaging.

Figure 30:
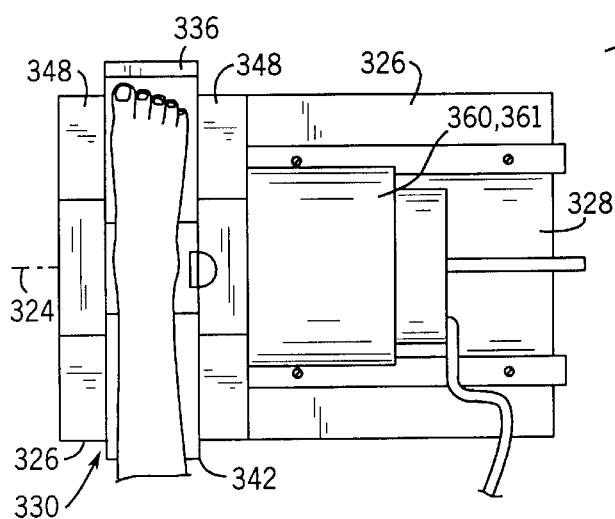
FIG. 30 is a top plan view of the cradle of FIG. 28 but with the foot positioner in use with a patient's leg and showing the use of an auxiliary pancake image intensifier for use with fluoroscopy or other x-ray equipment not having suitable dual energy or digital imaging capabilities.

Referring now to FIG. 27 and 30, the channel 330, extending substantially perpendicularly to axis 324 and has a horizontal bottom surface 333 pierced by two vertically extending guide holes 334 which may be used to receive and position corresponding pins 337 on one of two limb positioners 332. A foot positioner 336, as shown in FIG. 26, provides a padded calf support plate 338 fitting adjacent to the bottom surface 333 and an upwardly extending sole support 340 forming an obtuse angle with respect to the calf support plate 338. A cushion 342 on the calf support plate 338 may be adjusted so as to allow the patient's leg to extend upward somewhat from vertical for comfort. Gussets 344 span the angle between the sole plate 340 and calf support plate 338 to fix them in relative position but include apertures 346 to allow for the free passage of x-rays through a portion along axis 324 where the os calcis of the heal will be located.

When positioned within the channel 330, the foot positioner 336 is also supported by upwardly extending channel sidewalls 348 which serve further to provide an alignment surface for the imaging face of the image intensifier 320 or other detector array and on the other side, an alignment surface for an emitting face of the x-ray source 322. Channel sidewalls 348 are generally radio translucent so as to permit the passage of x-rays therethrough, but may include: calibration materials such as are well known in the art for calibrating dual energy devices, antiscatter grids also well known in the art, or occluders for evaluating scatter as have been described above or in the parent applications hereby incorporated by reference.

Figure 28:
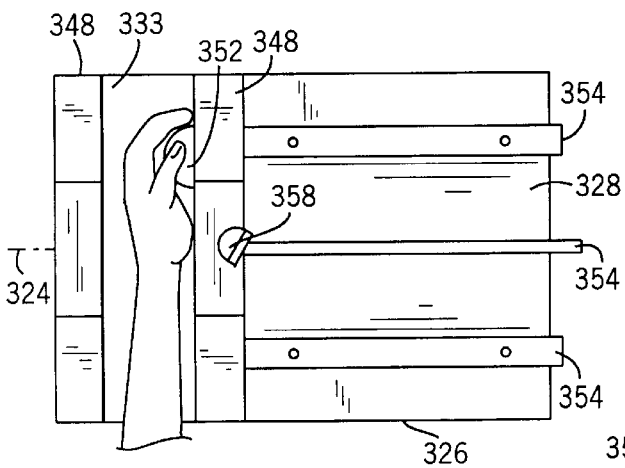
FIG. 28 is a top plan view of the cradle of FIG. 25 but with the C-arm removed, showing the forearm positioner in use with a patient's arm.

Referring to FIG. 27 and 28, for forearm imaging, the foot positioner 336 is removed and a palm support 352 is inserted by means of pin 337 in one of the holes 334 so as to locate a user's arm resting against the bottom surface 333 with the user's palm against the palm support 352 such that the bones of the forearm are placed along the axis 324 for imaging.

Figure 29:
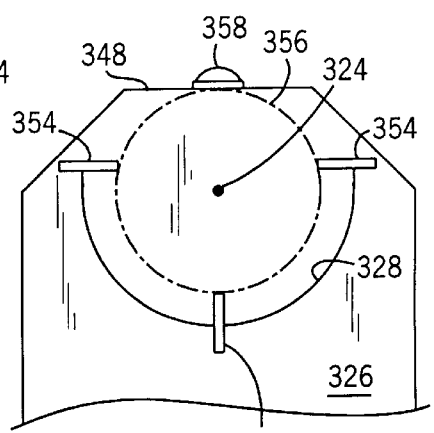
FIG. 29 is a side elevational view of the cradle of FIG. 28.

Referring to FIG. 28 and 29, the hemispherical support cradle 328 may include three radially inwardly extending ribs 354 attached by means of screws or the like to be replaceable. Two of the ribs 354 are positioned in a horizontal plane to substantially bisect the image intensifier 320 when it is placed within the cradle 328. The third rib 354 is positioned at the bottom of the cradle 328 and is opposed by a rotating locking collar 358 which may be used to further secure the image intensifier 320 within the cradle 328. The front edge of the image intensifier is abutted against the upright face of the dividing barrier so as to precisely locate it along axis 324. The inner edges of these ribs 354 define an inner radius 356 of lesser diameter than the cradle 328 that by proper design of the ribs 354 may be adjusted to conform to the outer surface of a particular image intensifier 320.

Referring now again to FIG. 30, some fluoroscopy equipment will not permit digital imaging or the necessary dual energy control needed for densitometry. Accordingly, an independent detector array 360 may be placed within the cradle 328 in lieu of the image intensifier 320. This detector array 360 may be a pair of stimulable phosphor plates as are understood in the art with intermediate filtering so as to provide dual energy readings with a polychromatic x-ray source. In this way a switching of voltage on the x-ray source 322, as described above, can be avoided. Alternatively, the detector array 360 may be a large area solid state detector or scanning detector assembly such as are understood in the art including those constructed of amorphous silicon and thin film transistor technology or those employing active pixel technology in which C-MOS integrated circuit fabrication techniques are employed. These detectors may be used with a switched x-ray source 322 to provide dual energy imaging or may be used in a stacked configuration with intermediate filtering so as to provide separate energy measurements, or may be used in a side-by-side configuration with interleaved detector elements filtered so as to be selectively sensitive to different energies.

Figure 31:
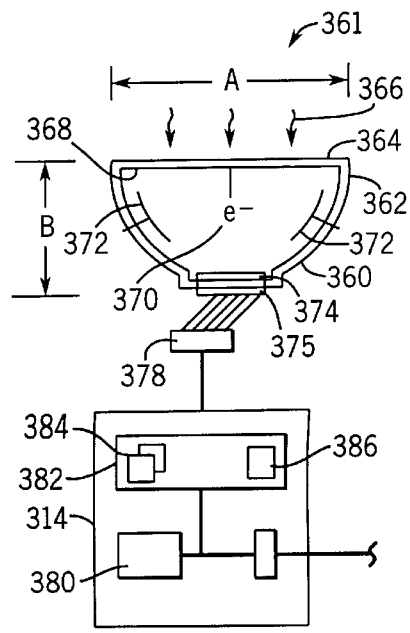
FIG. 31 is a cross sectional view of the pancake image intensifier of FIG. 30 with the protective shrouding removed and taken along a plane including the x-ray beam axis showing the compact, high distortion configuration and an attached processing computer.

In the preferred embodiment, and as shown in FIG. 31, the independent detector array 360 is a "pancake" image intensifier 361, suitably small so as to fit within the space between a conventional image intensifier 320 and the x-ray source 322. Referring to both FIG. 30 and 31, the pancake image intensifier 361 includes a vacuum bowl 362 having a planar front surface 364 for receiving x-rays 366 (normally through the channel sidewalls 348 of the stand 326).

According to conventional design, the x-rays 366 pass through the front surface 364 of the vacuum bowl 362 to strike a target material 368 to eject electrons 370 into the volume of the bowl 362. Focusing electrodes 372 direct the electrons to a phosphor 374 where an image is formed to be received by imaging array 375 such as a CCD array or camera. The image area of the phosphor 374 is much smaller than the front surface 364 so as to reduce the image size to one compatible with the camera. In the present invention the distance B between the target 368 and the imaging array 375 (including any optical path through one or more focusing lenses) is less than or equal to the radial dimension. A of the front surface 364 gives the pancake image intensifier 361 an extremely short form factor suitable for practice with the present invention.

Hitherto, such form factors were avoided because they are known to result in severe distortion of the image formed on the phosphor 374. This distortion is accommodated in the present invention by means of digital image processing in computer 314 which receives digitized pixel data from scanning electronics 378 connected to the imaging array 375 and corrects it according to the correction process described above with respect to the pin cushion correction. Accordingly, the addition of digital signal processing allows for production of pancake image intensifier 361 in which the separation of the imaging optics from the front of the image intensifier is much reduced.

The above adapter may be modified to use in femur imaging. In this case the 30 pedestal 326 may be eliminated in favor of a positioner (not shown) attached to the image intensifier 320 or x-ray source 322 directly. In the former case, the positioner may provide for a fixed air gap between the patient and the image intensifier 320 to reduce received scatter. So as to allow free manipulation of the C-arm 318, the positioner may be a lightweight plastic radiolucent material and may optionally include a calibration system such as a flip in phantom for calibration of the dual energy readings and occluders for scatter correction as has been described above. Collimation and/or a separate solid state dual energy image detectors may also be held by the positioner whose outer surface may guide the positioning of the C arm 318 to the necessary orientation which need not be horizontal but may be vertical for fore arm measurements or the like. For femur measurements, the patient may stand and the C-arm 318 manipulated appropriately as guided by the positioner.

Figure 32:
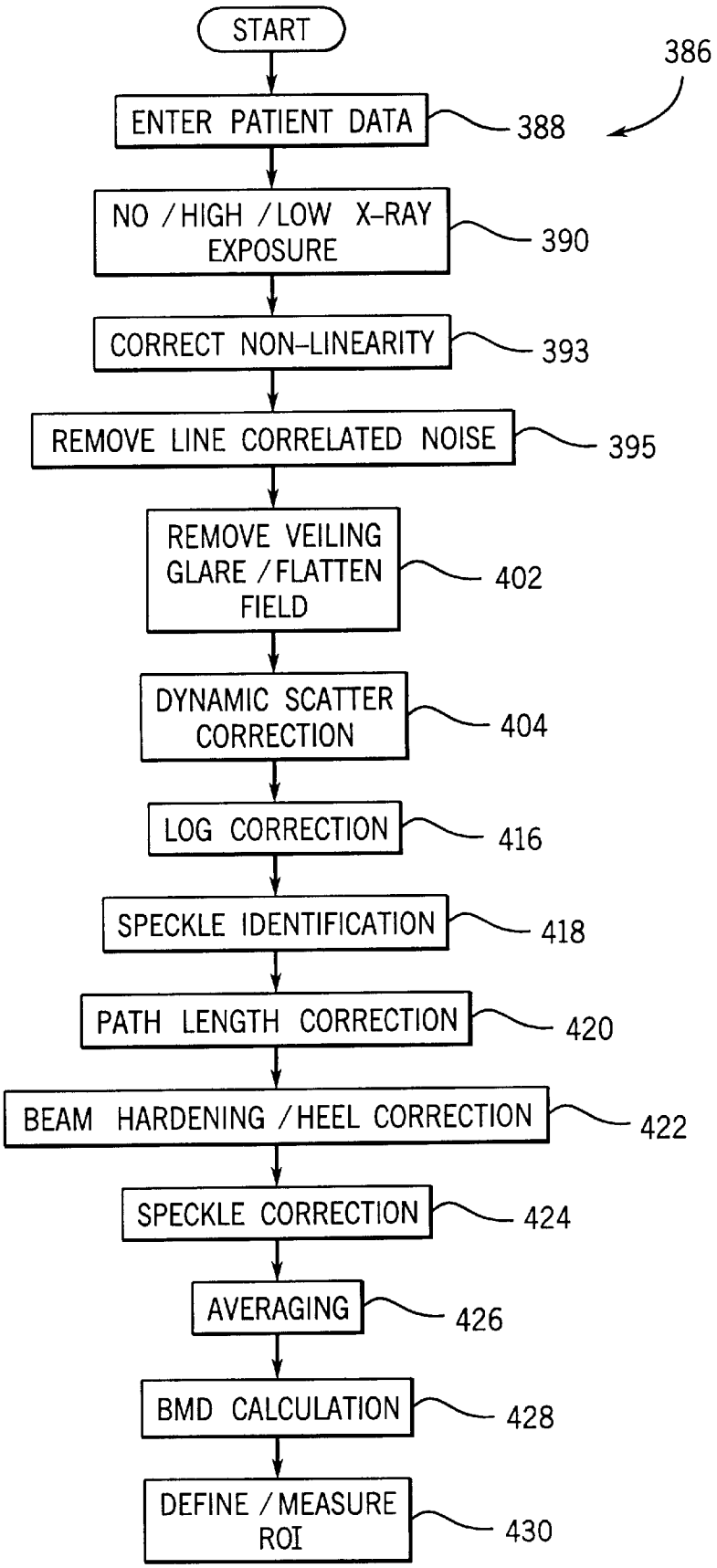
FIG. 32 is a flow chart of software executed by a processing computer associated with the -x-ray detector for providing quantitative densiometric data.

Referring now to FIG. 31 and 32, computer 314 includes a processor 380 and memory 382, the latter of which receives raw image data in the form of pixels having spatial locations and brightness values forming images 384. Memory 382 also includes a processing program 386 providing a general interface and control of the operation of the fluoroscopy machine 310 and a processing of images 384 so as to provide a quantitative measure of bone isolated from soft tissue.

The processing program 386 can be simply loaded into the computer 314 for the fluoroscopy machine 310 when the pedestal 326 is to be employed with a fluoroscopy machine 310 providing digital imaging and x-ray voltage control. If an independent detector array 360 is required, the program 386 may be executed on a computer 314 associated with that independent detector array 360.

At a first step in the program 386, indicated by process block 388, the operator of the fluoroscopy machine 310, having indicated a desire to perform densitometry and having positioned the C-arm in the pedestal 326, enters patient data that will be used to identify the image 384 to be collected.

At succeeding process block 390, data is collected for three distinct images 384 with: 1) no x-ray exposure, 2) high energy x-ray exposure, and 3) low energy x-ray exposure. Each of the exposures is preserved as a separate image file in the memory of the computer 314. The first exposure is used for correction routines to be described; the latter two exposures are used to deduce bone density according to methods well known in the art in which variations in high energy and low energy absorption are used to deduce the Compton scattering and atomic number of the material lying between the x-ray source 322 and the image intensifier 320. As is understood in the art, these two measurements allow the amount of bone as opposed to soft tissue located in that image region to be accurately measured. The data is acquired directly from the independent detector array 360 or in the event that stimulable plates are used, a reader may be attached to the computer 314 so as to acquire the necessary pixel data of an image 384. In the same way a conventional photographic film/filter plate arrangement may be used.

At next process block 393, each of these images is corrected for non-linearity of the detector such as may be determined empirically at an earlier time by testing the detector according to methods well known in the art, and which is a function of the detector and the technology used by the detector. Generally the testing exposes the detector to different fluences of x-rays and measures the output of the detector and the correction is intended to ensure that, for example, a doubling of fluence results in a doubling of detector output after correction. The correction is generally simply a scaling of each of the images by a factor that is a function of the pixel value for each pixel and possibly the location of the pixel.

Figure 34:
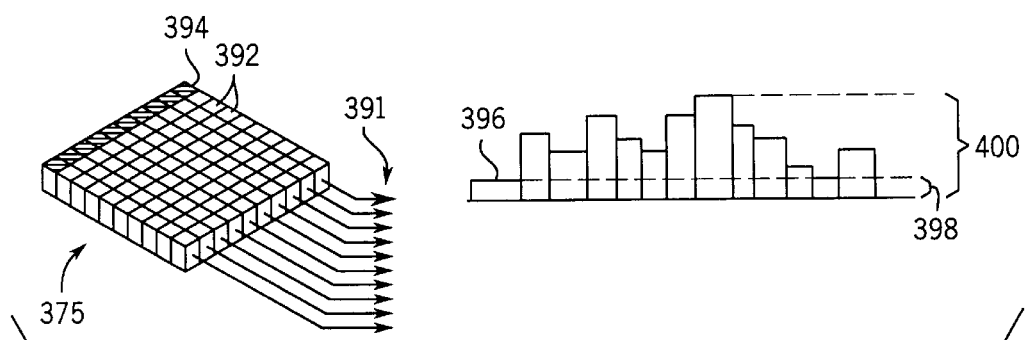
FIG. 34 is a block diagram illustrating the removal of line correlated noise per the present invention.

At process block 395, noise related to the particular line of the detector is removed. Referring to FIG. 34, the imaging array 375 provides a matrix of detector elements 392 arranged in rows and columns. Normally, either rows or columns are ganged together to be read out by dedicated read out electronics 391 spanning a particular row or column. The read out electronics introduces noise which is imposed upon each detector element 392 of that row and which is thus line correlated, that is, more highly correlated with other detector elements 392 of the line than detector elements 392 of different lines. To eliminate line correlated noise, one detector element 392 in each line is blocked by a lead mask 394 so as to be shielded from x-rays. A pixel value 396 from this blocked detector element 392 will provide a value that varies according to the line noise thus a line correlated noise value 398 may be deduced and subtracted from the pixel values 400 of the other detector elements 392 in the line.

Referring again to FIG. 32, at a succeeding process block 402, veiling glare is removed and the field is flattened. This former correction attempts to eliminate blurring of the image such as may be caused by scatter or similar effects within the imaging array 375. Glare refers generally to a reading that would be obtained under detector elements 392 that were wholly shadowed by an occluding absorber on the surface of the array 375. The glare is a function of the detector technology and is reduced by a deconvolution process based on an empirically derived deconvolution kernel according to a number of techniques well known in the art.

Also at process block 402 the field is flattened which is to say the gain variation of the detector elements 392 are normalized according to an empirically derived normalization map determined at the factory by exposing the detector to a uniform x-ray elimination and noting variation and intensities reported in the pixel values 400. At this time, dark currents from the detector elements 392 may also be eliminated as determined from the no-exposure x-ray image taken at process block 390.

Figure 33:
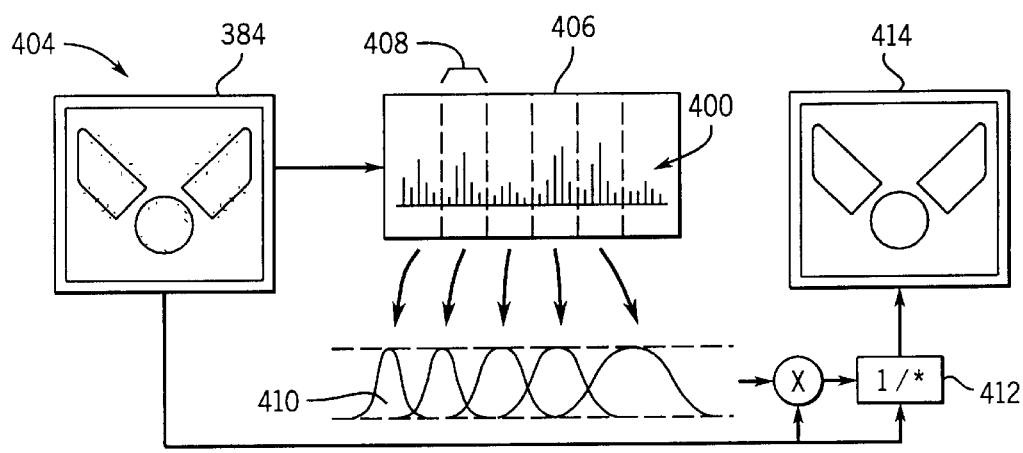
FIG. 33 is a block diagram of the steps of scatter correction of the present invention.

Referring now to process block 404, a dynamic scatter correction may be employed as has been previously described with respect to FIGS. 21–23. Alternatively referring also to FIG. 33, a dynamic scatter correction may be employed in which the data of the image 384 is analyzed so as to create a histogram 406 of pixel values 400 for the entire image. The histogram may be divided into regions 408 (five equal regions in the preferred embodiment) corresponding roughly x-ray paths through: 1) air-only, 2) thin tissue, 3) thick tissue only, 4) thin bone and, and 5) thick-bone. Each of these materials will exhibit a different scattering and hence a different empirically derived scatter kernel 410 may be assigned to each region 408 with generally the lower density regions having narrower kernels commensurate with less scatter.

The selected scatter kernel 410 may be scaled by the pixel value of the image 384 on a pixel by pixel basis and that kernel, so scaled, applied to a deconvolver 412 used to deconvolve the image 384 to produce a deconvolved image 414. A number of techniques of deconvolution are well known in the art using a fixed scatter kernel and these same techniques may be used with the variable scatter kernel 410 described here. During deconvolution the kernel 410 will be sequentially applied to a set of adjacent pixel values determined by the width of the kernel. The center pixel value at any step of the deconvolution will be used to scale the kernel and to identify the region of the histogram for the purpose of selecting the kernel 410. In an alternative embodiment, the kernel may be fixed and simply scaled by the value of the centermost pixel during de-convolution.

Referring again to FIG. 32, at process block 416, the images 384 are log corrected reflecting the fact that attenuation is exponentially related to thickness. The images are now related to thickness, a dimension which will be important in the ultimate bone-density determination.

At following process block 418, speckle may be identified for certain x-ray detectors 360 that are subject to extremely high readout values caused by noise which is possibly related to direct x-ray irradiation of the detector element. Speckle is identified by a simple thresholding process.

At next process block 420, path length correction may be performed based on the geometry of the particular C-arm such as may vary path length and magnification across the image as is well understood in the art.

Similarly at succeeding process block 422, beam hardening, the well known effect of a spectral shift in a polyenergetic x-ray beam as it passes through different thicknesses of material, and a Heel effect correction may be made, the Heel effect correction referring to a variation in the spectrum of an x-ray beam as a function of its angle in the cone of x-ray beams. Both of the corrections are known in the art, but must be employed in the present invention in order to provide suitable quantitative accuracy for densitometry.

At process block 424, the identified speckle of process block 418 is corrected by eliminating these identified pixels from subsequent calculation or by replacing them with a local average value.

The entire image may then be averaged or low-passed filtered at process block 426 so as to further reduce noise and to eliminate unneeded resolution.

The images are then processed according to well understood techniques to produce a bone mineral density value at process block 428. This bone mineral density value indicates the amount of bone material at each pixel of the image largely independent of surrounding soft tissue. The pixel image may be analyzed in a number of methods but most simply, as indicated by process block 430, by defining either automatically or manually a desired region of interest within the image and making a measurement of total bone density within that region. Automated techniques may look for a local maximum or minimum of bone density or may use image recognition type techniques to locate reproducibly a particular region of the forearm or os calcis. Morphometric analysis may be applied to the image to detect bone fracture and other techniques such as texture analysis may be performed according to methods well known in the art. The results of the analyses and images so processed may be displayed by the computer 314.

It is thus envisioned that the present invention is subject to many modifications which will become apparent to those of ordinary skill in the art. Accordingly, it is intended that the present invention not be limited to the particular embodiment illustrated herein, but embraces all such modified forms thereof as come within the scope of the following claim.

We claim:

1. A method of scatter correction for x-ray measurements comprising the steps of:
   (a) obtaining an x-ray measurement providing a plurality of x-ray attenuation values over an area;
   (b) preparing a histogram of the x-ray attenuation values, the histogram indicating the frequency of occurrence of attenuation values over a range of attenuations;
   (c) dividing the attenuation range into at least two regions corresponding to material types;
   (d) associating a different deconvolution kernel with each region; and
   (e) deconvolving the x-ray measurement with the different deconvolution kernels depending on the regions of the deconvolved attenuation values.

2. The method of claim 1 wherein the deconvolution kernels define a width of deconvolution measured as a number adjacent x-ray measurements within the deconvolution and wherein the different deconvolution kernels have different widths.

3. The method of claim 2 wherein the regions corresponding to greater attenuations, and hence to imaged materials having greater attenuation, are associated with deconvolution kernels having greater widths.

4. The method of claim 1 wherein the x-ray measurement is of a human and wherein the attenuation range is divided into regions corresponding to materials selected from the group consisting of: air-only, thin tissue, thick tissue only, thin bone and, and thick-only.

5. The method of claim 1 wherein the x-ray measurement is of a human and wherein the deconvolved x-ray measurement is further analyzed to provide a quantitative measurement of an imaged object.

6. The method of claim 5 wherein the quantitative measurement is an indication of bone density.

7. The method of claim 1 wherein during step (e) the deconvolution kernels are further weighted according to the intensity of the deconvolved attenuation values.

8. A method of scatter correction for x-ray measurements comprising the steps of:
   (a) obtaining an x-ray measurement providing a plurality of x-ray attenuation measurements over an area;
   (b) preparing at least one deconvolution kernel for scatter reduction in the x-ray measurements;
   (c) during the application of the deconvolution kernel to the x-ray measurements, applying a scale factor to the deconvolution kernel based on the value of the x-ray measurements being deconvolved.

9. The method of claim 8 wherein the x-ray measurement is of a human and wherein the deconvolved x-ray measurement is further analyzed to provide a quantitative measurement of an imaged object.

10. The method of claim 9 wherein the quantitative measurement is an indication of bone density.

* * * * *

UNITED STATES PATENT AND TRADEMARK OFFICE
CERTIFICATE OF CORRECTION

PATENT NO. : 6,215,846 B1
DATED : April 10, 2001
INVENTOR(S) : Richard B. Mazess et al.

It is certified that error appears in the above-identified patent and that said Letters Patent is hereby corrected as shown below:

Column 2,
Line 38, "amplified" should be -- simplified --.

Column 18,
Line 6, "the 30 pedestal" should be -- the pedestal --.

Signed and Sealed this

Eleventh Day of December, 2001

Attest:

NICHOLAS P. GODICI
*Attesting Officer*     *Acting Director of the United States Patent and Trademark Office*